(12) United States Patent
Zhang et al.

(10) Patent No.: US 8,244,350 B2
(45) Date of Patent: Aug. 14, 2012

(54) NEURAL STIMULATION FOR ARRHYTHMIA RECOGNITION AND THERAPY

(75) Inventors: Yunlong Zhang, Mounds View, MN (US); Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 304 days.

(21) Appl. No.: 12/535,332

(22) Filed: Aug. 4, 2009

(65) Prior Publication Data

US 2010/0036447 A1 Feb. 11, 2010

Related U.S. Application Data

(60) Provisional application No. 61/086,292, filed on Aug. 5, 2008.

(51) Int. Cl.
*A61N 1/00* (2006.01)
(52) U.S. Cl. .......................................................... 607/5
(58) Field of Classification Search ................ 607/4–28
See application file for complete search history.

(56) References Cited

U.S. PATENT DOCUMENTS

| | | | |
|---|---|---|---|
| 5,203,326 A | 4/1993 | Collins | |
| 5,578,061 A | 11/1996 | Stroetmann et al. | |
| 6,134,470 A | 10/2000 | Hartlaub | |
| 6,292,695 B1 | 9/2001 | Webster, Jr. et al. | |
| 6,567,691 B1 * | 5/2003 | Stadler ........................... | 600/515 |
| 6,611,713 B2 | 8/2003 | Schauerte | |
| 6,668,191 B1 | 12/2003 | Boveja | |
| 7,218,964 B2 | 5/2007 | Hill et al. | |
| 7,245,967 B1 | 7/2007 | Shelchuk | |
| 7,321,793 B2 | 1/2008 | Ben Ezra et al. | |
| 2002/0035335 A1 | 3/2002 | Schauerte | |
| 2002/0042630 A1 | 4/2002 | Bardy et al. | |
| 2002/0068958 A1 | 6/2002 | Bardy et al. | |
| 2002/0082658 A1 | 6/2002 | Heinrich et al. | |
| 2002/0103510 A1 | 8/2002 | Bardy et al. | |
| 2003/0181951 A1 | 9/2003 | Cates | |
| 2003/0212436 A1 | 11/2003 | Brown | |
| 2003/0236558 A1 | 12/2003 | Whitehurst et al. | |
| 2004/0193231 A1 | 9/2004 | David et al. | |
| 2004/0220629 A1 | 11/2004 | Kamath et al. | |
| 2005/0131464 A1 | 6/2005 | Heinrich et al. | |

(Continued)

FOREIGN PATENT DOCUMENTS

EP  0688577 A1  12/1995

(Continued)

OTHER PUBLICATIONS

"U.S. Appl. No. 11/538,488, Response filed Jan. 29, 2009 to Final Office Action mailed Oct. 29, 2008", 14 pgs.

(Continued)

*Primary Examiner* — Scott Getzow
(74) *Attorney, Agent, or Firm* — Schwegman, Lundberg & Woessner, P.A.

(57) ABSTRACT

A system and method can sense a tachyarrhythmia, compare the sensed tachyarrhythmia with a ventricular tachyarrhythmia criterion, provide a ventricular tachyarrhythmia therapy when the sensed tachyarrhythmia satisfies the ventricular tachyarrhythmia criterion, provide a neural stimulation when the sensed tachyarrhythmia does not satisfy the ventricular tachyarrhythmia criterion, determine whether the tachyarrhythmia continues during or after the neural stimulation when the tachyarrhythmia is sustained, compare the tachyarrhythmia sensed during or after the neural stimulation with a supraventricular tachyarrhythmia (SVT) criterion, and provide a ventricular tachyarrhythmia therapy when the sensed tachyarrhythmia does not satisfy the SVT criterion.

25 Claims, 8 Drawing Sheets

U.S. PATENT DOCUMENTS

| | | | |
|---|---|---|---|
| 2005/0131467 A1 | 6/2005 | Boveja | |
| 2005/0143776 A1 | 6/2005 | Brown | |
| 2006/0206154 A1 | 9/2006 | Moffitt et al. | |
| 2006/0253157 A1* | 11/2006 | Libbus et al. | 607/14 |
| 2007/0100380 A1 | 5/2007 | Fukui | |
| 2007/0179543 A1 | 8/2007 | Ben-David et al. | |
| 2007/0203527 A1 | 8/2007 | Ben-David et al. | |
| 2007/0260283 A1 | 11/2007 | Li | |
| 2008/0046016 A1 | 2/2008 | Ben-David et al. | |
| 2008/0086174 A1 | 4/2008 | Libbus et al. | |
| 2008/0269819 A1 | 10/2008 | Zhou | |

FOREIGN PATENT DOCUMENTS

| | | |
|---|---|---|
| EP | 0688578 A1 | 12/1995 |
| EP | 1304135 A2 | 4/2003 |
| JP | 08038626 | 2/1996 |
| JP | 2004351122 A | 12/2004 |
| WO | WO-00/27474 A1 | 5/2000 |
| WO | WO-0027474 A1 | 5/2000 |
| WO | WO-2006039694 A2 | 4/2006 |
| WO | WO-2006/098996 A1 | 9/2006 |
| WO | WO-2006/121836 A1 | 11/2006 |
| WO | WO-2007/133877 A2 | 11/2007 |
| WO | WO-2008/042468 A2 | 4/2008 |

OTHER PUBLICATIONS

"U.S. Appl. No. 11/538,488, Non-Final Office Action mailed on Oct. 29, 2008", 19 pgs.

"PCT Application No. PCT/US2007/066741, International Search Report mailed Jan. 30, 2008", 4 pgs.

"PCT Application No. PCT/US2007/066741, Written Opinion mailed Jan. 30, 2008", 8 pgs.

Ando, M., et al., "Efferent Vagal Nerve Stimulation Protects Heart Against Ischemia-Induced Arrhythmias by Preserving Connexin43 Protein", *Circulation*, 112(2), (Jul. 12, 2005), 164-170.

Libbus, I., et al., "System for Neurally-Mediated Anti-Arrhythmic Therapy", U.S. Appl. No. 11/538,488, filed Oct. 4 2006, 37 pgs.

Murakawa, Y., et al., "Effect of Cervical Vagal Nerve stimulation on Defibrillation Energy: a Possible Adjunct to Efficient Defibrillation", *Japanese Heart Journal*, 44(1), (Jan. 2003), 91-100.

Shelchuk, A. M, et al."Reduced defibrillation energy by vagal stimulation", (Abstract No. 328), *Europace Supplements*, vol. 7, No. S1, (2005), 105-106.

Takahashi, N, "Vagal Modulation of Ventricular Tachyarrhythmias Induced by Left Ansae Subclaviae Stimulation in Rabbits", *Japanese Heart Journal*, 39(4), (Jul. 1998), 503-511.

Vanoli, E., et al., "Vagal Stimulation and Prevention of Sudden Death in Conscious Dogs with a Healed Myocardial Infarction", *Circulation Research*, 68(5), (1991), 1471-1481.

Zamotrinsky, A. V., et al., "Vagal neurostimulation in patients with coronary artery disease.", *Autonomic Neuroscience*, 88(1-2), (Apr. 12, 2001), 109-116.

"U.S. Appl. No. 11/382,120, Non-Final Office Action mailed Nov. 27, 2009.", 11 pgs.

"U.S. Appl. No. 11/382,120 Final Office Action mailed Jul. 8, 2010", 12 pgs.

"U.S. Appl. No. 11/382,120, Response filed Mar. 29, 2010 to Non Final Office Action mailed Nov. 27, 2009", 13 pgs.

"U.S. Appl. No. 11/382,120, Response filed Sep. 8, 2010 to Final Office Action mailed Jul. 8, 2010", 14 pgs.

U.S. Appl. No. 11/382,120, Response filed Sep. 30, 2009 to Restriction Requirement, mailed Sep. 4, 2009, 10 pgs.

"U.S. Appl. No. 11/382,120, Resriction Requirement mailed Sep. 4, 2009", 5 pgs.

"Japanese Application Serial No. 2009-509919, Amended Claims filed Feb. 10, 2010", (w/ English Translation of Amended Claims), 11 pgs.

"U.S. Appl. No. 11/382,120, Advisory Action mailed Jan. 31, 2012", 3 pgs.

"U.S. Appl. No. 11/382,120, Advisory Action mailed Oct. 1, 2010", 6 pgs.

"U.S. Appl. No. 11/382,120, Examiner Interview Summary mailed Aug. 11, 2011", 4 pgs.

"U.S. Appl. No. 11/382,120, Final Office Action mailed Oct. 28, 2011", 8 pgs.

"U.S. Appl. No. 11/382,120, Non Final Office Action mailed Mar. 30, 2011", 14 pgs.

"U.S. Appl. No. 11/382,120, Response filed Aug. 4, 2011 to Non Final Office Action mailed Mar. 30, 2011", 13 pgs.

"U.S. Appl. No. 11/382,120, Response filed Dec. 28, 2011 to Final Office Action mailed Oct. 28, 2011", 11 pgs.

"European Application Serial No. 07760739.8, Examination Notification Art. 94(3) mailed May 16, 2011", 4 pgs.

"European Application Serial No. 07760739.8, Examination Notification Art. 94(3) Response Filed Oct. 26, 2011", 15 pgs.

"Japanese Application Serial No. 2009-509919, Office Action mailed Jan. 20, 2012", (w/ English Translation), 5 pgs.

* cited by examiner

NEURAL STIMULATION FOR ARRHYTHMIA RECOGNITION AND THERAPY

CROSS-REFERENCE TO RELATED APPLICATION

This application claims the benefit of U.S. Provisional Application No. 61/086,292, filed on Aug. 5, 2008, under 35 U.S.C. §119(e), which is hereby incorporated by reference.

BACKGROUND

Cardiac arrhythmias can result in a range of uncomfortable and life-threatening conditions for patients. A normally-functioning heart relies on coordinated delays in the propagation of electrical impulses through cardiac tissue. Blocked or abnormal electrical conduction through cardiac tissue can cause dysynchronous contraction, and can reduce hemodynamic efficiency and cardiac output. Deteriorated cardiac tissue can encourage arrhythmic behavior and can result in compromised blood supply to the heart, and to the rest of the body, as well as the possibility of thromboembolism, stroke, or even death.

Tachyarrhythmias can be thought of as abnormal heart rhythms characterized by a too-rapid heart rate. Examples of ventricular tachyarrhythmias include ventricular tachycardia (VT), and ventricular fibrillation (VF). Ventricular arrhythmias can be caused by waves of depolarization propagating through cardiac tissues of differing electrical characteristics (e.g., differences in propagation delay, refractory time). A self-sustaining reentrant depolarization wave with one or more foci can usurp control of heart rate from the sino-atrial (SA) node. Such reentrancy can allow the ventricular contraction rate to run away, resulting in abnormally fast, unco-ordinated, and inefficient ventricular contractions, such as in the case of VT. Anti-tachyarrhythmia pacing (ATP) therapy, ventricular shock therapy, or a combination can be provided by a cardiac rhythm management device to restore a normal sinus rhythm before the VT degenerates into life-threatening VF.

VF can be occurring if no identifiable QRS complexes or coordinated contractions of the ventricles are present. Shock therapy from, for example, an automated implantable cardioverter defibrillator (AICD), cardiac resynchronization therapy device with defibrillation backup (CRT-D), or an external defibrillator can be provided to convert the VF to a normal sinus rhythm.

OVERVIEW

Supraventricular tachyarrhythmias (SVTs) occur in regions of the heart other than the ventricles, and can originate in either the atrioventricular (AV) node or at a location in the atria. SVTs can be less likely than VT or VF to result in patient death. However, SVTs can still result in significant patient discomfort and elevated stroke risk. SVTs can be relatively common in patients suffering from heart disease.

Examples of SVTs include atrial flutter (AFL), atrial fibrillation (AF), atrioventricular reciprocating tachycardia (AVRT), and AV-nodal reentrant tachycardia (AVNRT).

Atrial flutter can be associated with a rapid atrial contraction rate, for example, up to approximately 250-350 beats-per-minute (BPM). Atrial flutter can be associated with the formation of one or more "circus" pathways around the atrium, with the resulting atrial tissue activations occurring at a far higher rate than as directed by the SA node. During an episode of atrial flutter, the AV node can inhibit the transmission of impulses associated with the high atrial contraction rate, resulting in a lower rate of ventricular contractions (e.g., the observed ventricular rate can be below the atrial rate or a lack exists of a one-to-one correspondence between atrial and ventricular events).

Atrioventricular reciprocating tachycardia (AVRT) can be similar to atrial flutter, but can involve a reentrant circuit following both a normal conduction pathway between the atria and the ventricles, as well as an abnormal accessory pathway to complete the circuit.

AV-nodal reentrant tachycardia (AVNRT) can be similar to AVRT, but can involve the reentrant circuit following a path through or near the AV node, as well as an accessory path to complete the circuit.

Both AVRT and AVNRT can exhibit either antegrade (e.g., normal or "forward" conduction) or retrograde conduction (e.g., depolarization travels opposite its normal direction) through the normal path.

If multiple uncoordinated pathways form, and a predominant reentrant circuit can be absent, atrial fibrillation (AF) can be occurring. Unlike VF, AF need not be life threatening since the AV node can block conduction of high-rate uncoordinated atrial events. The resulting intrinsic ventricular contractile behavior can provide adequate hemodynamic margin to sustain the life of the patient.

Management and treatment of SVTs varies and can include, for example, IV medications, Vasalva maneuver, and carotid massage. Such treatments can trigger a parasympathetic reflex (e.g., vagal reflex). This can increase the refractory period of a portion of the reentry circuit, which can disrupt the tachyarrhythmic "circus" wavefront, thereby either regulating or terminating the tachyarrhythmia.

Electrical, optical or acoustic stimulation of neural targets (e.g., for either parasympathetic stimulation or sympathetic inhibition) can similarly help modify or terminate the tachyarrhythmia modification.

Discrimination between VT, VF, and SVTs can allow a cardiac rhythm management (CRM) system or health care practitioner to provide life-critical VT or VF therapy when needed. Identifying an arrhythmia as a type of SVT, rather than as VT or VF, can reduce the likelihood of administering a painful and potentially ineffective shock to a conscious patient. In the case of an implantable battery-powered CRM device, reducing inappropriate shocks can also extend battery life, thereby increasing the time before explant and replacement is needed, with its accompanying risks, including infection.

Discrimination between various types of SVTs can also be used to select a therapy more likely to terminate or regulate a specific subclass of SVT.

For example, if an SVT can be classified as AF, then one or more devices (e.g., an implantable CRM and neural stimulation device) can respond with, for example, neural stimulation, and an optional atrial shock. If an SVT can be classified as AFL, then a device can respond with, for example, neural stimulation, and an optional anti-tachyarrhythmia pacing (ATP) protocol. Thus, when AF and AFL can be distinguished from each other, unnecessary atrial shock therapy can be suppressed.

In various examples, among other things, the present systems or methods can provide a diagnostic neural stimulation protocol at the onset of an arrhythmia such as to elicit a change in a measurable physiological parameter, such as heart rate.

In various examples, among other things, the present systems or methods can classify a tachyarrhythmia as either a ventricular tachyarrhythmia (e.g., VT or VF), or an SVT (e.g., AF or AFL), such as based on the observed change in heart rate resulting from a diagnostic neural stimulation. In various examples, among other things, the present systems or methods can subclassify an SVT as AF, AFL, or a reentrant SVT.

Example 1 comprises a system. In this example, the system includes a sensing input configured to sense a tachyarrhythmia; a rhythm sensor coupled to the sensing input, the rhythm sensor configured to: compare a sensed tachyarrhythmia with a ventricular tachyarrhythmia criterion; compare a sustained tachyarrhythmia with a supraventricular tachyarrhythmia (SVT) criterion when the tachyarrhythmia continues during or after a neural stimulation; a ventricular tachyarrhythmia therapy generator, coupled to the rhythm sensor, configured to: provide a ventricular tachyarrhythmia therapy when the sensed tachyarrhythmia satisfies the ventricular tachyarrhythmia criterion; provide a ventricular tachyarrhythmia therapy when the sensed tachyarrhythmia does not satisfy the SVT criterion; and a neural stimulation generator, coupled to the rhythm sensor, configured to provide a neural stimulation when the sensed tachyarrhythmia does not satisfy the ventricular tachyarrhythmia criterion.

In Example 2, the system of Example 1 optionally comprises a system wherein the ventricular tachyarrhythmia criterion included in the rhythm sensor includes at least one comparator selected from the list of: (1) a heart rate threshold comparator, coupled to the sensing input; (2) a heart rate acceleration comparator, coupled to the sensing input; (3) a morphological feature comparator, coupled to the sensing input; and (4) an R-R interval variance comparator, coupled to the sensing input.

In Example 3, the system of at least one of Examples 1-2 optionally comprises a system wherein: (1) the heart rate threshold comparator is configured to compare a sensed heart rate with a heart rate threshold value, wherein the heart rate threshold comparator is configured to declare a probable ventricular tachyarrhythmia when the heart rate threshold is met or exceeded continuously during an interval equal to or longer than a timeout limit; (2) the heart rate acceleration comparator is configured to compare a sensed heart rate acceleration with a heart rate acceleration threshold value, wherein the heart rate acceleration comparator is configured to declare a probable ventricular tachyarrhythmia when the heart rate acceleration threshold is met or exceeded; (3) the morphological feature comparator is configured to compare a sensed tachyarrhythmia with an electrogram morphological feature template, wherein the comparator is configured to declare a probable ventricular tachyarrhythmia when the morphological feature comparison threshold is met or exceeded; and (4) the R-R interval variance comparator is configured to compare the variance of a population of sensed R-R intervals with a stability threshold variance, wherein the comparator is configured to declare a probable ventricular tachyarrhythmia when the stability threshold variance is not met or exceeded by the variance of a population of sensed R-R intervals.

In Example 4, the system of at least one of Examples 1-3 optionally comprises a system wherein the sensing input is configured to sense an atrial event rate and a ventricular event rate, and wherein the SVT criterion included in the rhythm sensor comprises an event rate comparator, coupled to the sensing input, the event rate comparator configured to declare the SVT criterion as satisfied by the sensed tachyarrhythmia when a sensed atrial event rate is greater than or equal to a sensed ventricular event rate by a specified amount.

In Example 5, the system of at least one of Examples 1-4 optionally comprises a system wherein the sensing input is configured to sense an atrial event and a ventricular event, and wherein the SVT criterion included in the rhythm sensor comprises a one-to-one correspondence detector, coupled to the sensing input, the one-to-one correspondence detector configured to declare the SVT criterion as satisfied by the sensed tachyarrhythmia when a one-to-correspondence between an atrial event and a ventricular event is detected.

In Example 6, the system of at least one of Examples 1-5 optionally comprises a rhythm sensor configured to trend a cardiac event rate over time, wherein the rhythm sensor includes an SVT discriminator, the SVT discriminator configured to: classify an SVT as a probable reentrant SVT when a rate trend corresponds to a reentrant SVT criterion; classify an SVT as probable atrial flutter (AFL) when the rate trend corresponds to an atrial flutter criterion; and classify an SVT as atrial fibrillation (AF) when the rate trend corresponds to an atrial fibrillation criterion.

In Example 7, the system of at least one of Examples 1-6 optionally comprises a system wherein the SVT discriminator is configured to sense a termination of a tachyarrhythmia during or after a neural stimulation.

In Example 8, the system of at least one of Examples 1-7 optionally comprises an SVT discriminator including a probable reentrant SVT criterion, the SVT discriminator comprising: a heart rate threshold comparator, coupled to the sensing input, configured to compare a sensed heart rate with a heart rate threshold value, and wherein the heart rate threshold comparator is configured to classify an SVT as a probable reentrant SVT when, after a neural stimulation, the sensed heart rate is below the heart rate threshold value; a therapy decision unit, coupled to the SVT discriminator, configured to select a neural stimulation protocol for terminating the probable reentrant SVT, in response to the classification of an SVT as a probable reentrant SVT; and a neural stimulation generator, coupled to the therapy decision unit, configured to deliver the selected neural stimulation protocol.

In Example 9, the system of at least one of Examples 1-8 optionally comprises an SVT discriminator including a probable atrial flutter criterion, the SVT discriminator comprising: a heart rate ratio comparator, coupled to the sensing input, configured to compare a computed ratio of two sensed heart rates with a threshold ratio value, the two sensed heart rates sampled after a neural stimulation, and wherein the heart rate ratio comparator is configured to classify an SVT as a probable atrial flutter when the computed ratio is below the threshold ratio value.

In Example 10, the system of at least one of Examples 1-9 optionally comprises a therapy decision unit, coupled to the SVT discriminator, configured to select a neural stimulation protocol for terminating the probable atrial flutter and to optionally select an anti-tachyarrhythmia pacing (ATP) protocol for terminating the probable atrial flutter, in response to the classification of an SVT as a probable atrial flutter; a neural stimulation generator, coupled to the therapy decision unit, configured to deliver the selected neural stimulation protocol; and an ATP stimulation generator, coupled to the therapy decision unit, configured to optionally deliver the selected ATP protocol.

In Example 11, the system of at least one of Examples 1-10 optionally comprises an SVT discriminator including a probable atrial fibrillation criterion, the SVT discriminator comprising: a heart rate ratio comparator, coupled to the sensing input, configured to compare a computed ratio of two sensed heart rates with a threshold ratio value, the two sensed heart rates sampled after a neural stimulation, and wherein the heart rate ratio comparator is configured to classify an SVT as a probable atrial fibrillation when the computed ratio is at or above the threshold ratio value.

In Example 12, the system of at least one of Examples 1-11 optionally comprises a therapy decision unit, coupled to the SVT discriminator, configured to select a neural stimulation protocol for terminating the probable atrial fibrillation and to optionally select an atrial shock protocol for terminating the probable atrial fibrillation, in response to the classification of an SVT as a probable atrial fibrillation; a neural stimulation generator, coupled to the therapy decision unit, configured to deliver the selected neural stimulation protocol; and an atrial shock generator, coupled to the therapy decision unit, configured to optionally deliver the selected atrial shock protocol.

Example 13 describes a method. In this example, the method comprises: sensing a tachyarrhythmia; comparing the sensed tachyarrhythmia with a ventricular tachyarrhythmia criterion; providing a ventricular tachyarrhythmia therapy when the sensed tachyarrhythmia satisfies the ventricular tachyarrhythmia criterion; providing a neural stimulation when the sensed tachyarrhythmia does not satisfy the ventricular tachyarrhythmia criterion; determining whether the tachyarrhythmia continues during or after the neural stimulation when the tachyarrhythmia is sustained; comparing the tachyarrhythmia sensed during or after the neural stimulation with a supraventricular tachyarrhythmia (SVT) criterion; and providing a ventricular tachyarrhythmia therapy when the sensed tachyarrhythmia does not satisfy the SVT criterion.

In Example 14, the method of Example 13 optionally comprises a method wherein satisfying the ventricular tachyarrhythmia criterion includes satisfying at least one criterion selected from the list of: (1) a heart rate threshold criterion; (2) a heart rate acceleration criterion; (3) an electrogram morphological feature template criterion; and (4) an R-R interval stability criterion.

In Example 15, the method of at least one of Examples 13-14 optionally comprises a method wherein (1) the heart rate threshold criterion comprises: establishing a heart rate threshold; comparing a sensed heart rate to the heart rate threshold; triggering a timer when the patient heart rate meets or exceeds the heart rate threshold; establishing a timeout limit; comparing an elapsed time indicated by the timer with the timeout limit; declaring the sensed tachyarrhythmia as a probable ventricular tachyarrhythmia when the heart rate threshold is met or exceeded continuously during an interval equal to or longer than the timeout limit; (2) the heart rate acceleration criterion comprises: establishing a heart rate acceleration threshold; comparing a sensed heart rate acceleration to the heart rate acceleration threshold; declaring the sensed tachyarrhythmia as a probable ventricular tachyarrhythmia when the heart rate acceleration threshold is met or exceeded; (3) the electrogram morphological feature template criterion comprises: establishing an electrogram morphological feature template for ventricular tachyarrhythmia; establishing a morphological comparison threshold; comparing the sensed tachyarrhythmia to the electrogram morphological feature template; declaring the sensed tachyarrhythmia as a probable ventricular tachyarrhythmia when the morphological comparison threshold is met or exceeded; and (4) the R-R interval stability criterion comprises: sensing a series of R-R intervals; extracting a variance of a population of sensed R-R intervals; establishing a stability threshold variance; comparing the variance of the population of sensed R-R intervals to the stability threshold variance; and declaring the sensed tachyarrhythmia as a probable ventricular tachyarrhythmia when the variance of a population of sensed R-R intervals fail to meet or exceed the stability threshold variance.

In Example 16, the method of at least one of Examples 13-15 optionally comprises a method wherein satisfying the SVT criterion includes sensing an atrial event rate greater than or equal to a ventricular event rate.

In Example 17, the method of at least one of Examples 13-16 optionally comprises a method wherein satisfying the SVT criterion includes sensing a substantially one-to-one correspondence between an atrial event and a ventricular event.

In Example 18, the method of at least one of Examples 13-17 optionally comprises trending a heart rate over time; classifying an SVT as a probable reentrant SVT when the heart rate trend corresponds to a reentrant SVT criterion; classifying an SVT as probable atrial flutter (AFL) when the heart rate trend corresponds to an atrial flutter criterion; and classifying an SVT as atrial fibrillation (AF) when the heart rate trend corresponds to an atrial fibrillation criterion.

In Example 19, the method of at least one of Examples 13-18 optionally comprises a system wherein the reentrant SVT criterion includes sensing a termination of a tachyarrhythmia during or after the providing the neural stimulation.

In Example 20, the method of at least one of Examples 13-19 optionally comprises: selecting a neural stimulation protocol configured for terminating the probable reentrant SVT; providing a neural stimulation selected configured for terminating the probable reentrant SVT when the reentrant sensed tachyarrhythmia satisfies the SVT criterion; wherein the reentrant SVT criterion includes: establishing a lower threshold value for the heart rate; sampling the heart rate at a specified time after the providing the neural stimulation; comparing the sampled heart rate with the lower threshold value; and detecting the sampled heart rate below the lower threshold value.

In Example 21, the method of at least one of Examples 13-20 optionally comprises a method wherein the probable atrial flutter criterion includes: establishing a threshold ratio value for the heart rate; sampling the heart rate at two specified times; dividing a later sample of the value of the heart rate by an earlier sample of the value of the heart rate to establish a computed ratio; comparing the computed ratio with the threshold ratio value; and detecting a ratio below the threshold ratio value.

In Example 22, the method of at least one of Examples 13-21 optionally comprises: selecting a neural stimulation protocol for terminating the probable atrial flutter; providing a therapeutic neural stimulation selected for terminating the probable atrial flutter when the sensed tachyarrhythmia satisfies the probable atrial flutter criterion; and optionally providing anti-tachyarrhythmia pacing (ATP) for terminating the probable atrial flutter when the sensed tachyarrhythmia satisfies the probable atrial flutter criterion.

In Example 23, the method of at least one of Examples 13-22 optionally comprises a method wherein the probable atrial fibrillation criterion includes: establishing a threshold ratio value for the heart rate; sampling the heart rate at two specified times; dividing a later sample of the value of the heart rate by an earlier sample of the value of the heart rate to establish a computed ratio; comparing the computed ratio with the threshold ratio value; and detecting a ratio at or above the threshold ratio value.

In Example 24, the method of at least one of Examples 13-23 optionally comprises: selecting a neural stimulation protocol for terminating the probable atrial fibrillation; and providing a therapeutic neural stimulation selected for terminating the probable atrial fibrillation when the sensed tachyarrhythmia satisfies the probable atrial fibrillation criterion; and optionally providing atrial shock therapy for terminating the probable atrial fibrillation when the sensed tachyarrhythmia satisfies the probable atrial fibrillation criterion.

Example 25 describes a machine readable medium including instructions that, when performed by the machine, cause the machine to: sense a tachyarrhythmia; compare the sensed tachyarrhythmia with a ventricular tachyarrhythmia criterion; provide a ventricular tachyarrhythmia therapy when the sensed tachyarrhythmia satisfies the ventricular tachyarrhythmia criterion; provide a neural stimulation when the sensed tachyarrhythmia does not satisfy the ventricular tachyarrhythmia criterion; determine whether the tachyarrhythmia continues during or after the neural stimulation when the tachyarrhythmia is sustained; compare the tachyarrhythmia sensed during or after the neural stimulation with a supraventricular tachyarrhythmia (SVT) criterion; and provide a ventricular tachyarrhythmia therapy when the sensed tachyarrhythmia does not satisfy the SVT criterion.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Cardiac rate, contractility and excitability can be modulated through central nervous system mediated reflex pathways, which can include portions of the sympathetic and parasympathetic components of the autonomic nervous system. For example, baroreceptors and chemoreceptors in the heart, great vessels, and lungs can transmit cardiac activity information through parasympathetic and sympathetic afferent nervous fibers to the central nervous system. Increase of sympathetic afferent activity can trigger reflex sympathetic activation, parasympathetic inhibition, blood vessel constriction, and tachycardia. In contrast, parasympathetic activation can result in bradycardia, blood vessel dilation, and inhibition of vasopressin release.

The balance between the sympathetic and parasympathetic components of the autonomic nervous system can be referred to as the autonomic tone. Decreased parasympathetic or vagal tone can be a factor that can contribute to or cause various cardiac tachyarrhythmias. Such tachyarrhythmias can include atrial fibrillation and ventricular tachycardia, for example. The present inventors have recognized, among other things, that neural stimulation can be used to elicit the reflex response of parasympathetic activation or of sympathetic inhibition, and that information about this response can be used to distinguish or discriminate between various cardiac arrhythmias.

Figure 1:
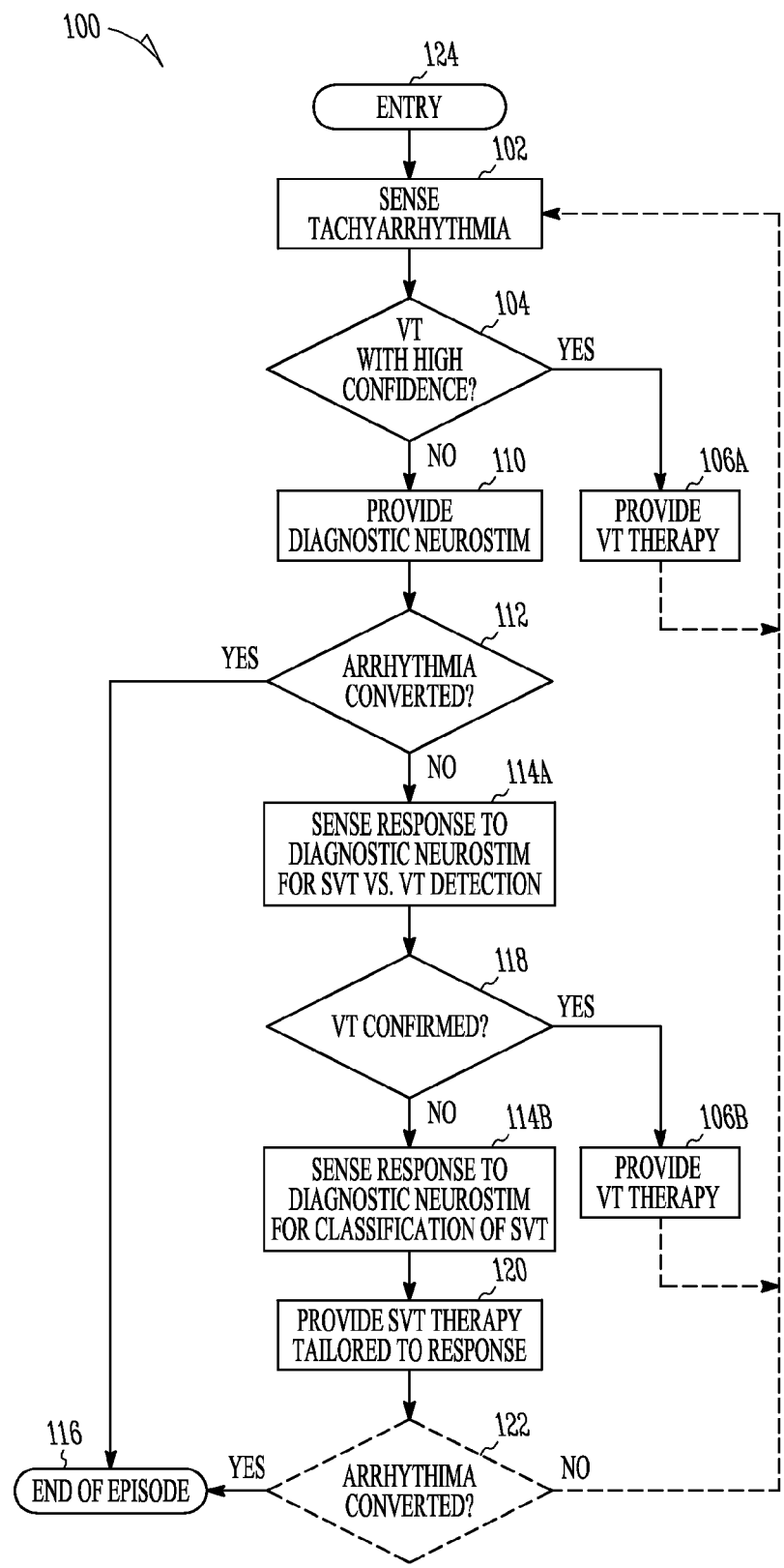
FIG. 1 is a diagram illustrating generally an example of at least a portion of a process that can include a diagnostic neural stimulation to aid in discrimination between various cardiac arrhythmias.

FIG. 1 is a diagram illustrating generally an example of at least a portion of a process 100 that can include a neural stimulation 110 to elicit a response that can be used to help discriminate between various cardiac arrhythmias. Such a process can, for example, be performed using a cardiac rhythm management system with neural stimulation capability. For example, at 124, a cardiac rhythm management system can perform a process 100 to sense and treat an arrhythmia. At 102, an arrhythmia can be sensed, for example, by processing a digital representation of an electrocardiogram obtained from either an implanted cardiovascular lead or measured on the surface of a patient's skin. At 104, it can be determined whether the detected arrhythmia can be ascertained with high confidence as a ventricular tachyarrhythmia, and the outcome of that determination can be used to determine later acts to be performed.

Figure 9:
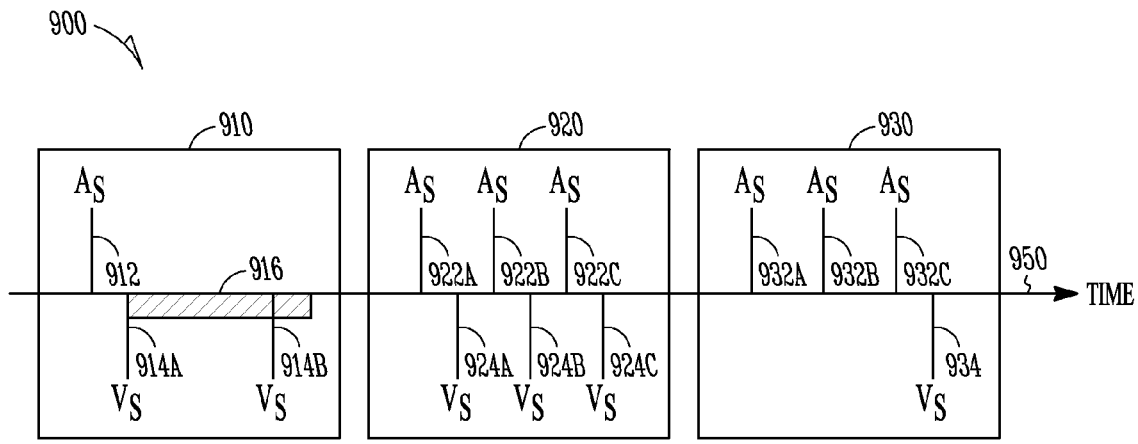
FIG. 9 is a diagram illustrating generally an example of at least a portion of an event timeline indicating, not to scale, the relative order of atrial and ventricular sensed events according to various arrhythmia detection scenarios.

In some arrhythmias, the relationship between sensed atrial events and sensed ventricular events can be used to discriminate between ventricular tachyarrhythmias and SVTs. FIG. 9 illustrates some examples of discriminating between ventricular tachyarrhythmias and SVTs using atrial and ventricular event relationships.

In some examples, high confidence of ventricular tachyarrhythmia can be achieved by comparing a sensed tachyarrhythmia with one or more ventricular tachyarrhythmia criteria (e.g., if one or more such ventricular tachyarrhythmia criteria are met, the arrhythmia can be characterized as a probable ventricular tachyarrhythmia).

By way of example, a ventricular tachyarrhythmia criterion can include a specified ventricular heart rate upper threshold value. When a ventricular heart rate meets or exceeds the threshold value, a timer can be started. If the ventricular heart rate stays at or above the threshold value for longer than a timer-indicated limit, then this ventricular tachyarrhythmia criterion can be declared as satisfied.

At 104, when the ventricular tachyarrhythmia can be detected, with high confidence, then a ventricular tachyarrhythmia therapy can be provided at 106A. Examples of such tachyarrhythmia therapy can include, but are not limited to, ventricular shock, ventricular anti-tachyarrhythmia pacing (ATP), or a combination of both.

In some examples, a ventricular tachyarrhythmia criterion includes a specified heart rate acceleration criterion. When a change in ventricular rate meets or exceeds a heart rate acceleration threshold value, then this ventricular tachyarrhythmia criterion can be declared as satisfied. A heart rate acceleration can be determined as a change in heart rate when heart rate is measured at two or more times. In the time domain, a heart rate acceleration can be determined as a change in a beat-to-beat interval measured between one pair of successive heart beats versus another. This change can be computed from a sampled beat-to-beat interval, or, for example, from an average (or other central tendency) of several samples of beat-to-beat intervals. A negative change in beat-to-beat interval indicates an accelerating heart rate.

In some examples, a ventricular tachyarrhythmia criterion includes an electrogram morphological feature template criterion. A stored morphological feature template can be used to establish characteristic morphological features, such as associated with ventricular depolarizations occurring during one or more ventricular tachyarrhythmias. A morphological comparison can use a correlation analysis between a sensed electrocardiogram (electrogram) and the morphological feature template. A correlation threshold value can be established. If the correlation between the sensed electrogram and the morphological feature template results in a correlation value that meets or exceeds the correlation threshold value, then this ventricular tachyarrhythmia criterion can be declared as satisfied.

In some examples, a ventricular tachyarrhythmia criterion includes an R-R interval stability criterion. A series of ventricular contractions can be detected as R-waves sensed from an electrogram. A statistical variance or other measure of dispersion of the population of sensed R-R intervals can be extracted, such as by using a numerical approximation. A dispersion threshold value can be established. If the measured dispersion of the population of sensed R-R intervals fails to meet or exceed the specified dispersion threshold value, then this ventricular tachyarrhythmia criterion can be declared as satisfied.

In certain examples, multiple ventricular tachyarrhythmia criteria can be combined, such as by a weighted linear or other combination of various of the above individual ventricular tachyarrhythmia criteria.

If, after detection at 104, the tachyarrhythmia has been converted to normal sinus rhythm at 122 by ventricular tachyarrhythmia therapy provided at 106A, then the CRM system can declare an end of the tachyarrhythmia episode at 116 and can resume normal ambulatory functioning.

If, at 104, the arrhythmia cannot be determined to be a ventricular tachyarrhythmia with high confidence, then, at 110, a neural stimulation can be provided, for diagnostic purpose, such as to a vagus nerve, a cardiac branch of the vagus nerve, a cardiac fat pad, a baroreceptor site, or to one or more other neural targets that stimulate the parasympathetic nervous system or inhibit the sympathetic nervous system, or both.

If, at 112, the arrhythmia has been converted or has spontaneously terminated, the CRM system can declare an end of the arrhythmia episode at 116. In certain examples, the CRM system can log the arrhythmia as a possible AVNRT or AVRT as a result of the conversion detected at 112 after delivering a neural stimulation at 110.

At 114A, the CRM system can sense a response to a diagnostic neural stimulation to detect whether the arrhythmia as either a probable ventricular tachyarrhythmia or an as-yet unclassified SVT. Similar to 104, at 118, when a ventricular tachyarrhythmia can be confirmed, ventricular therapy can be provided at 106B.

At 114B, the CRM system can sense a response to the diagnostic neural stimulation to classify an SVT as a probable reentrant SVT (e.g., AVNRT or AVRT), probable AFL or probable AF, such as by comparing the response to the neural stimulation to a reentrant SVT criterion, an atrial flutter criterion, or an atrial fibrillation criterion. A response to the neural stimulation can include, for example, one or more of a change in heart rate, a change in timing between an atrial and a ventricular contraction (atrio-ventricular delay), a change in timing between successive atrial or ventricular events, a change in atrial or ventricular morphology as indicated by an electrogram, or the like. In certain examples at least one of a reentrant SVT criterion, an atrial flutter criterion, or an atrial fibrillation criterion can be a heart rate threshold.

In certain examples, a single instance of providing diagnostic neural stimulation, such as, for example, at 110, can be used for subsequent sensed response analysis at 114A, 114B. In other examples, multiple diagnostic neural stimulations an be used, such as before both 114A and 114B.

At 120, an SVT therapy can be selected using the classification result from 114B. At 122, if the arrhythmia continues, all or part of the detection, classification, therapy selection, and therapy delivery process can optionally be repeated.

Figure 2:
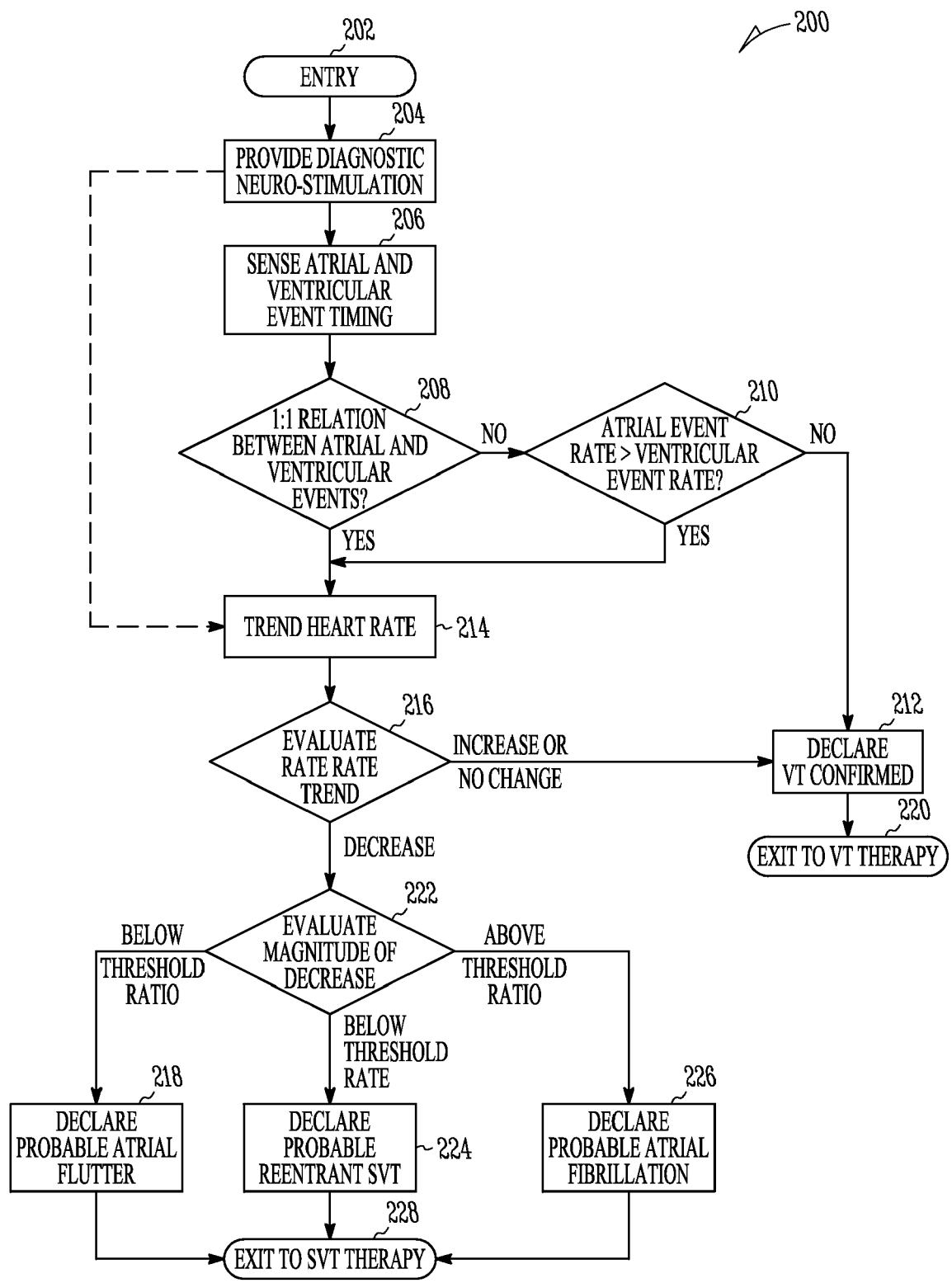
FIG. 2 is a diagram illustrating generally an example of at least a portion of a process that can include a diagnostic neural stimulation to aid in discrimination between various cardiac arrhythmias, and that can include a method to discriminate between probable atrial fibrillation and probable atrial flutter based on a change in heart rate associated with a diagnostic neural stimulation.

FIG. 2 is a diagram illustrating generally an example of at least a portion of a process 200 that can include a diagnostic neural stimulation 204 to help discriminate between various cardiac arrhythmias, such as between probable atrial fibrillation 226 and probable atrial flutter 218 based on a change in heart rate in response to the diagnostic neural stimulation 204.

Such a process can use a cardiac rhythm management system with neural stimulation capabilities. For example, at 202, a cardiac rhythm management system can enter a process 200 to discriminate between various arrhythmias.

At 204, a diagnostic neural stimulation can be provided. In some examples, at 206, the relationship between sensed atrial events and sensed ventricular events can be evaluated to discriminate between ventricular tachyarrhythmias and SVTs. At 208, if a one-to-one (1:1) correspondence or relationship between atrial sensed events and ventricular sensed events occurs, the process can proceed to 214 for further classification of a probable SVT. In some examples, a one-to-one correspondence occurs when, during a sensed interval, for each atrial event sensed, a corresponding ventricular event follows the atrial event, with no intervening atrial events.

In some examples, SVT classification can begin without requiring detection of whether a 1:1 relationship exists between atrial and ventricular events. A delivery of diagnostic neural stimulation at 204 can be made without requiring discrimination between an SVT and VT at 208, 210, by proceeding directly to establishing a rate trend at 214 after diagnostic neural stimulation at 204 (e.g., some atrial arrhythmias might not exhibit a consistent 1:1 relationship, but can still exhibit a detectable rate-change response).

For various arrhythmias, the atrial and ventricular events can exhibit a relationship that is not 1:1. For example, at 210, if the atrial sensed event rate appears greater than the ventricular sensed event rate, for example, by at least a specified margin or threshold, the process can still proceed to 214 for further classification since a high atrial sensed event rate without a corresponding 1:1 ventricular sensed rate can still indicate an SVT.

If the sensed ventricular rate appears greater than the sensed atrial rate, for example, by at least a specified margin or threshold, then, at 212, a probable ventricular tachyarrhythmia can be declared. At 220, the SVT classification process can then proceed to a separate process to provide ventricular tachyarrhythmia therapy.

If either a 1:1 relationship between atrial and ventricular sensed events is detected 208, or if an atrial sensed event rate exceeds a ventricular sensed event rate 210, then a rate trend can be established at 214. This can involve monitoring or analyzing a series of beat-to-beat intervals between atrial or ventricular sensed events recorded by the CRM system before, just after, and well after delivering a diagnostic neural stimulation at 204 (e.g., monitoring or analyzing "just after" can involve recording a change in heart rate occurring within two or more heartbeats after delivering the diagnostic neural stimulation).

In some examples, at 214 a rate trend can be established by sampling and storing different beat-to-beat intervals between sensed ventricular, sensed atrial events, or a combination of the two. A moving or other average or other central tendency of heart rate (or inversely, intervals), or atrio-ventricular delay (AVD), can be used, such as to reduce the sensitivity of the process to spurious beat-to-beat variations, for example, by sampling several beat-to-beat intervals and averaging the results to form a given sample.

At 216, a rate trend can be evaluated, such as to help classify an SVT. For example, an increasing rate, or no change in the heart rate during or after the neural stimulation at 204 can result in declaring a ventricular tachyarrhythmia at 212, triggering a separate ventricular tachyarrhythmia therapy process at 220.

If delivering the diagnostic neural stimulation at 204 decreases the heart rate, a lower rate threshold value can be established, and after the neural stimulation at 204, if the heart rate is less than or equal to this threshold value, a probable reentrant SVT can be declared at 224.

In some examples, a ratio can be computed between the heart rates just after and just before the diagnostic neural stimulation at 204, and the computed ratio can be compared to a specified ratio threshold value at 222. A probable atrial fibrillation can be declared when the computed ratio meets or exceeds the threshold value at 226. A probable atrial flutter can be declared at 218 when the computed ratio is less than the specified threshold value.

In some examples, the atrial flutter is declared when the computed ratio is less than or equal to the threshold value, and atrial fibrillation is declared when the computed ratio exceeds the threshold value.

At 222, the magnitude of the heart rate decrease can be evaluated well after delivering a diagnostic neural stimulation (e.g., several heartbeats later or several tens of beats later) at 204. This can help increase confidence in an SVT classification. Atrial fibrillation can be associated with a gradual decrease in heart rate after delivering the diagnostic neural stimulation at 204. In some examples, a probable atrial fibrillation can be declared with greater confidence at 226 when two or more successive heart rate samples result in a computed ratio that exceeds a specified ratio threshold value, wherein the ratio is computed with respect to a heart rate sample occurring before delivering the diagnostic neural stimulation at 204.

At 228, an appropriate SVT therapy can be selected and optionally delivered after an SVT has been classified at 218, 224, or 226.

Figure 3:
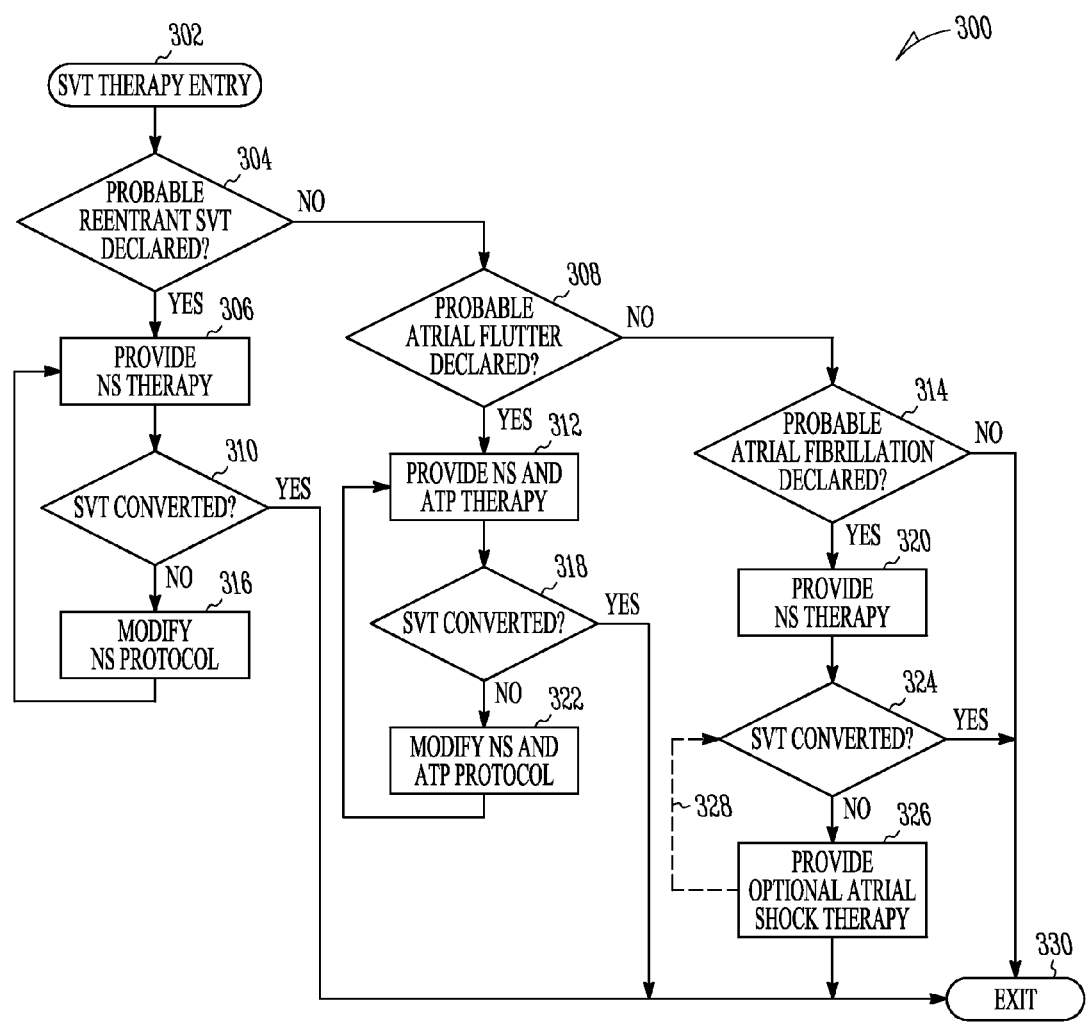
FIG. 3 is a diagram illustrating generally an example of at least a portion of a process that can include determining an SVT therapy protocol based upon a classification of an SVT.

FIG. 3 is a diagram illustrating generally an example of at least a portion of a process 300 that can include determining an SVT therapy protocol based upon a classification of an SVT into an appropriate sub-class of SVT. This can involve using a cardiac rhythm management system with neural stimulation capabilities. For example, at 302, a cardiac rhythm management system can enter a process 300 to select and provide one or more SVT therapies.

For example, at 304, if a probable reentrant SVT has been declared, then a therapeutic neural stimulation tailored to terminate the reentrant SVT can be provided at 306. In some examples, neural stimulation therapy can be applied iteratively. If an SVT termination is sensed at 310, then the process can exit at 330, such as to resume normal ambulatory functioning.

If the SVT continues at 310, the therapeutic neural stimulation protocol can be repeated at 306, or optionally modified at 316 and then applied in modified form at 306. Modification at 316 can include programming or otherwise altering one or more neural stimulation parameters such as amplitude, frequency, burst frequency, burst duration, duty cycle, morphology, pulse width, or the like.

Modification at 316 can be performed in a closed-loop fashion, such as by using as a control input a sample of a physiologic parameter such as heart rate before, during, or after delivery of the therapeutic neural stimulation.

In some examples, if a probable atrial flutter is declared at 308, one or more of anti-tachyarrhythmia pacing (ATP) or neural stimulation can be provided at 312. If the SVT is not converted at 312, then, one or more of the neural stimulation or ATP protocols can be optionally modified at 322 for iteratively providing therapy at 312. In some examples, the ATP can be provided before, during, or after the neural stimulation therapy at 312.

In some examples, if probable atrial fibrillation has been declared at 314, neural stimulation can be provided at 320, either alone or together with (ATP). If the atrial fibrillation is not terminated, atrial shock therapy can be optionally provided at 326. Atrial shock can be painful to a conscious patient. In some examples, clinician, physician or a patient confirmation can be used to determine whether to deliver an atrial shock at 326, or whether to deliver subsequent atrial shocks at 328 if the atrial fibrillation continues.

In some examples, at 310, 318, 324, an SVT can be reclassified and the appropriate therapy branch can be selected for subsequent therapy instances and can include one or more ventricular tachyarrhythmia therapies when a ventricular tachyarrhythmia is detected. In this way, ventricular tachyarrhythmia detection/discrimination and treatment can continue to operate concurrently with SVT discrimination/discrimination and treatment to enhance patient safety.

Figure 4:
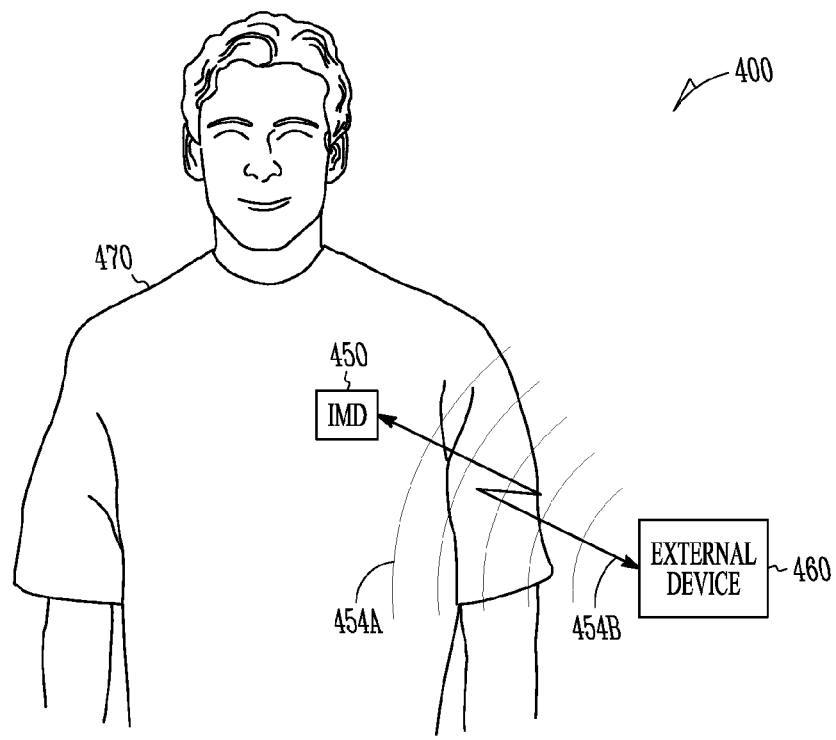
FIG. 4 is a diagram illustrating generally an example of at least a portion of a system that can include an implantable medical device (IMD), implanted within a patient, coupled to an external device.

FIG. 4 is a diagram illustrating generally an example of at least a portion of a system 400 that can include an implantable medical device (IMD) 450, which can be implanted within a patient 470 and wirelessly coupled by a communication or power link 454A-B to an external device 460, and optionally further communicatively coupled to a centralized server or other remote external device.

In some examples, the IMD 450 can include at least one neural stimulation generator configured to stimulate the parasympathetic system or inhibit the sympathetic system. In some examples, the IMD 450 can also include one or more of a cardiac rhythm management CRM therapy delivery circuit and a cardiac or other physiological signal sensing circuit, such as to provide pacing-level electrostimulation therapy (e.g., for one or more of bradycardia pacing or cardiac resynchronization therapy (CRT)), or a shock therapy circuit.

The cardiac or other physiological signal sensing circuit can be included in the external device 460, such as within a piece of hospital equipment, a bedside device, or a clinician programmer. For example, such an external device 460 can be equipped with surface electrogram (ECG) sensing capability coupled to the patient 470.

In some examples, the external device 460 can communicate wirelessly 454B with one or more IMDs 450 such as to transmit or receive one or more of diagnostic, control, or information messages, or the like. Examples of wireless communication 454B can include one or more of acoustic, magnetic, electromagnetic, optical, or body conduction techniques.

In some examples, the external device 460 can supply some or all operating energy to the IMD 450 through a wireless transduction scheme 454A such as described with respect to 454B. The operating energy 454A can be supplied concurrently with one or more communication signals 454B (e.g., a carrier signal can be rectified to recover energy 454A, and modulation of the carrier signal can allow for information transfer 454B), or through a separate and distinct technique. In some examples, an IMD 450 can be equipped with multiple wireless transduction schemes using different energy transmission mechanisms 454A-B, such as, for example, a combination of two or more transducers using sound, magnetic coupling, electromagnetic radiation, optical radiation, or conduction through patient tissue.

Figure 5:
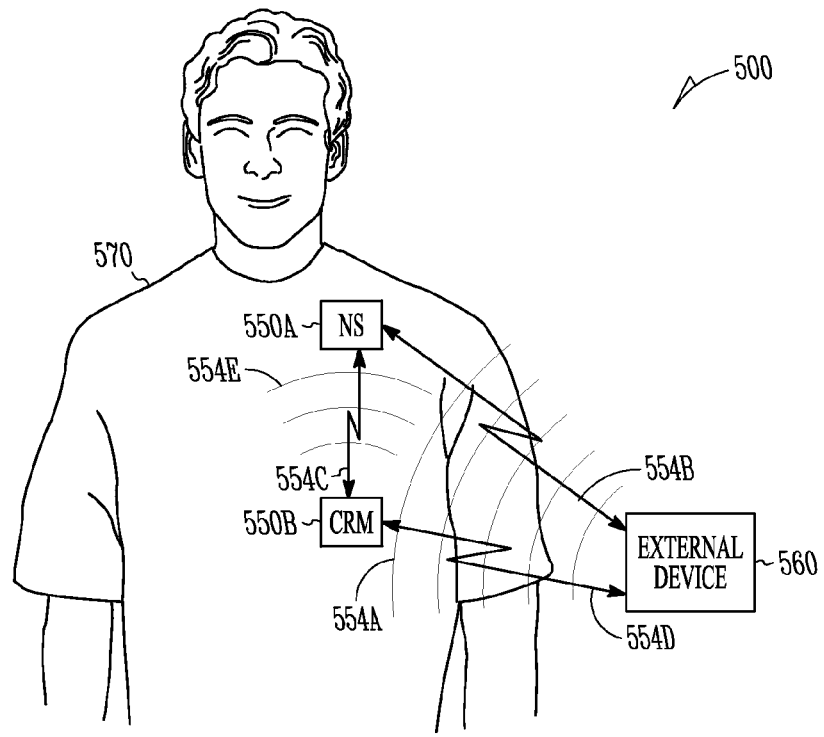
FIG. 5 is a diagram, similar to FIG. 4, illustrating generally an example of at least a portion of a system that can include two implantable medical devices (IMDs), implanted within a patient, coupled to an external device.

FIG. 5 is a diagram, similar to FIG. 4, illustrating generally an example of at least a portion of a system 500 that can include two implantable medical devices (IMDs), 550A-B, implanted within a patient 570, coupled to an external device 560. In some examples, at least one implantable neural stimulation device 550A can be implanted at a location to facilitate delivery of neural stimulation.

At least one CRM device 550B, can be implanted at a location within the patient 470 to facilitate cardiac event sensing, and cardiac therapy delivery such as cardiac pacing or shock. CRM device 550B implant locations within the patient 570 can, for example, be subcutaneous, submuscular, intravascular, intracardiac or a combination of such locations (e.g., a CRM device can include both a pulse generator assembly and one or more lead assemblies).

As discussed above for FIG. 4, the CRM device 550B can be or include one or more portions external to the patient in some examples. The external device 560, can communicate wirelessly 554B, 554D with, for example, one or more of the neural stimulation implant 550A, or the CRM device, 550B. In some examples, operating energy 554A, can be supplied to either 550A, 550B, or a combination of the two. In some examples, a wired or wireless communication link 554C can be formed between a neural stimulation implant 550A and the CRM device 550B. In some examples, a CRM device 550B can wirelessly supply operating energy 554E to a neural stimulation implant 550A.

Figure 6:
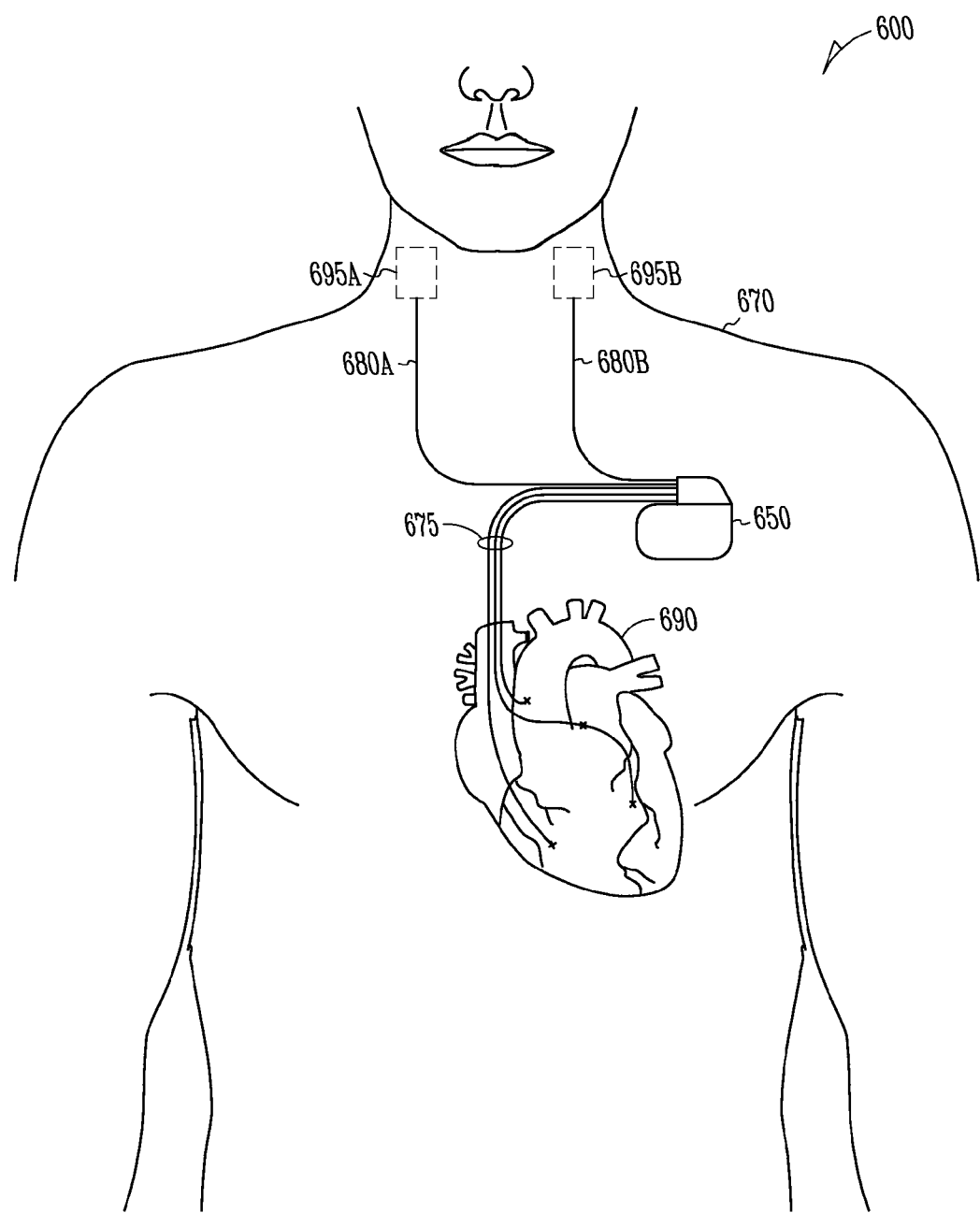
FIG. 6 is a diagram illustrating generally an example of at least a portion of a system that can include an IMD, implanted within a patient, that can include lead(s) positioned to provide CRM therapy to a heart, and can include leads positioned to stimulate a vagus nerve, by way of example, but not by way of limitation, according to various embodiments.

FIG. 6 is a diagram illustrating generally an example of at least a portion of a system 600 that can include an IMD 650, implanted within a patient 670, that can include lead(s) 675 positioned to provide CRM therapy to a heart 690, and can include one or more leads 680A-B positioned to stimulate one or more neural targets 695A-B. In some examples, the IMD 650 can contain both a neural stimulation generator, coupled to leads 680A-B, and a CRM therapy and sensing circuit coupled to one or more leads 675.

In some examples, leads 680A-B can be subcutaneously tunneled or intravascularly fed to a location near one or more neural targets 695A-B.

In some examples, leads 680A-B can include, along their length or at an end distal to an IMD 650, or both, one or more cuffs that can be configured to partially or completely encircle a neural target 695A-B. A portion of the cuff can include one or more transducers to stimulate the neural target 695A-B such as by using electrical (e.g., conductive, magnetic, or electromagnetic), acoustic (e.g., ultrasound), or optical stimulation, or any combination.

In some examples, one or more of leads 680A-B can include along their length or at an end distal to an IMD 650, or both, one or more transducers configured to transvascularly stimulate a neural target 695A-B such as by using electrical, acoustic (e.g., ultrasound), or optical stimulation, or a combination, such as through the blood vessel wall. In some examples, a vagal neural target 695A-B can be stimulated by one or more leads 680A-B positioned within the internal jugular vein such as to elicit predominantly parasympathetic activity (e.g., at a vagal neural target 695A-B) or to inhibit a sympathetic response (e.g., at a baroreceptor neural target 695A-B, such as at or near the pulmonary artery).

Figure 7:
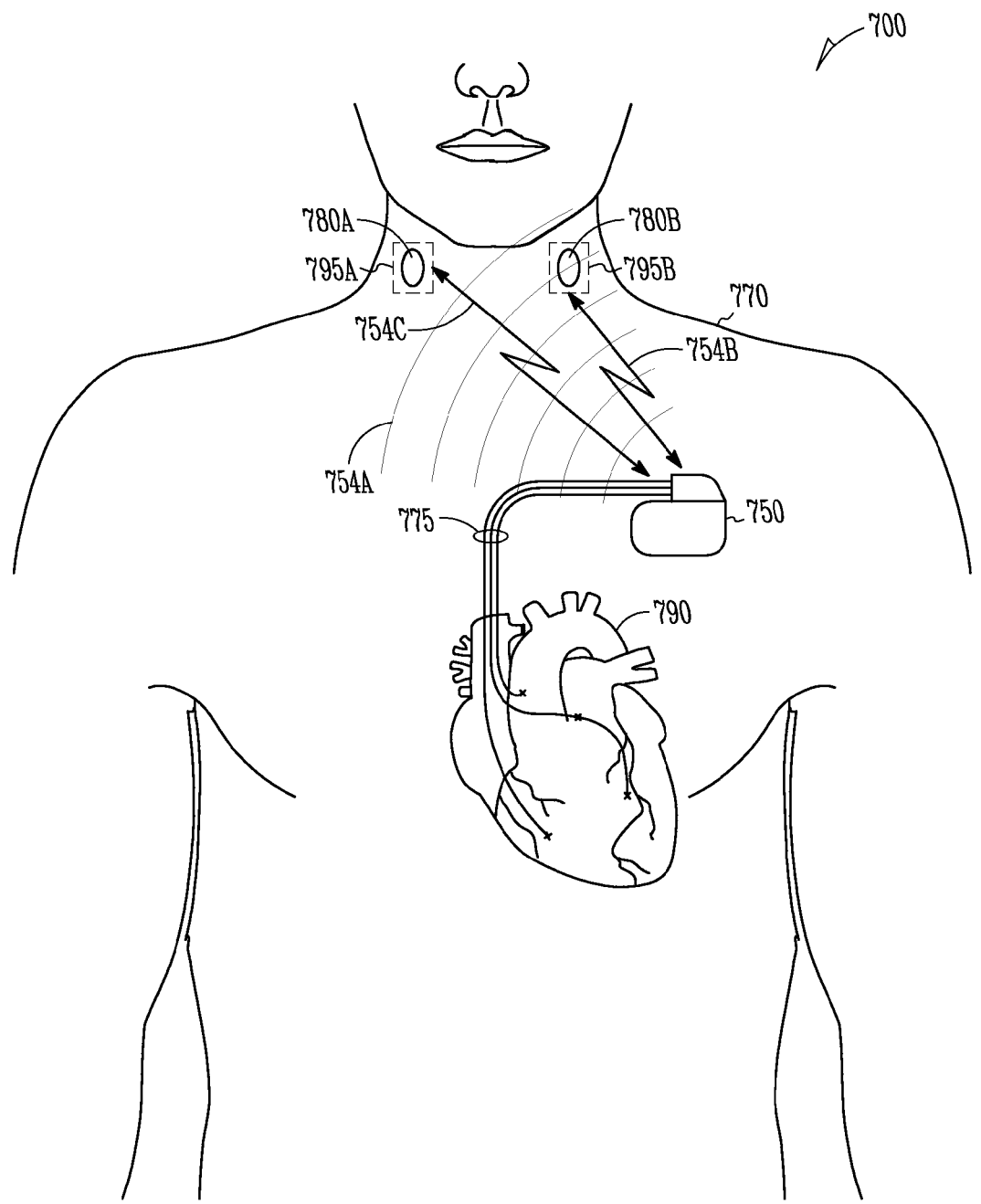
FIG. 7 is a diagram, similar to FIG. 6, illustrating generally an example of at least a portion of system that can include an IMD, implanted within a patient, that can include lead(s) positioned to provide CRM therapy to a heart, and with satellite transducers positioned to stimulate at least one neural target.

FIG. 7 is a diagram, similar to FIG. 6, illustrating generally an example of at least a portion of system that can include an IMD 750, implanted within a patient 770, that can include lead(s) 775 positioned to provide CRM therapy to a heart 790, and with one or more satellite neural stimulation transducers 795A-B positioned to stimulate one or more neural targets 780A-B. Satellite transducers ("seeds") 795A-B can be intravascularly, subcutaneously, or otherwise positioned near one or more neural targets 780A-B similarly to the locations described for neural stimulation lead 680A-B terminations in the context of FIG. 6. In some examples, IMD 750 can be equipped with a transmitter or transceiver such as to wirelessly communicate 754B-C with seeds 795A-B. Such wireless communication can be used, in certain examples, for communication of one or more of control, status, diagnostic, or information messages between IMD 750 and one or more seeds 795A-B. Wireless communication energy 754B-C can be generated or received such as by one or more of acoustic, magnetic (e.g., inductive), electromagnetic (e.g., radiative non-optical), optical, or body conduction transduction arrangements.

In some examples, the IMD 750 can supply operating energy to one or more of the seeds 780A-B such as through a wireless transduction scheme 754A similar to that discussed in the context of FIG. 4. The operating energy 754A can be supplied concurrently with one or more communication signals 754B-C (e.g., a carrier signal can be rectified at one or more of seeds 780A-B to recover energy 754A, and modulation of the carrier signal can allow for information transfer 754B-C), or through a separate and distinct technique.

In some examples, one or more of the seeds 780A-B can include a wireless receiver to receive one or more of communication 754B-C or operating energy signals 754A, but can omit a wireless transmitter. Power consumption, complexity, and physical volume of seed devices 780A-B can be reduced when a wireless transmitter is omitted.

Figure 8:
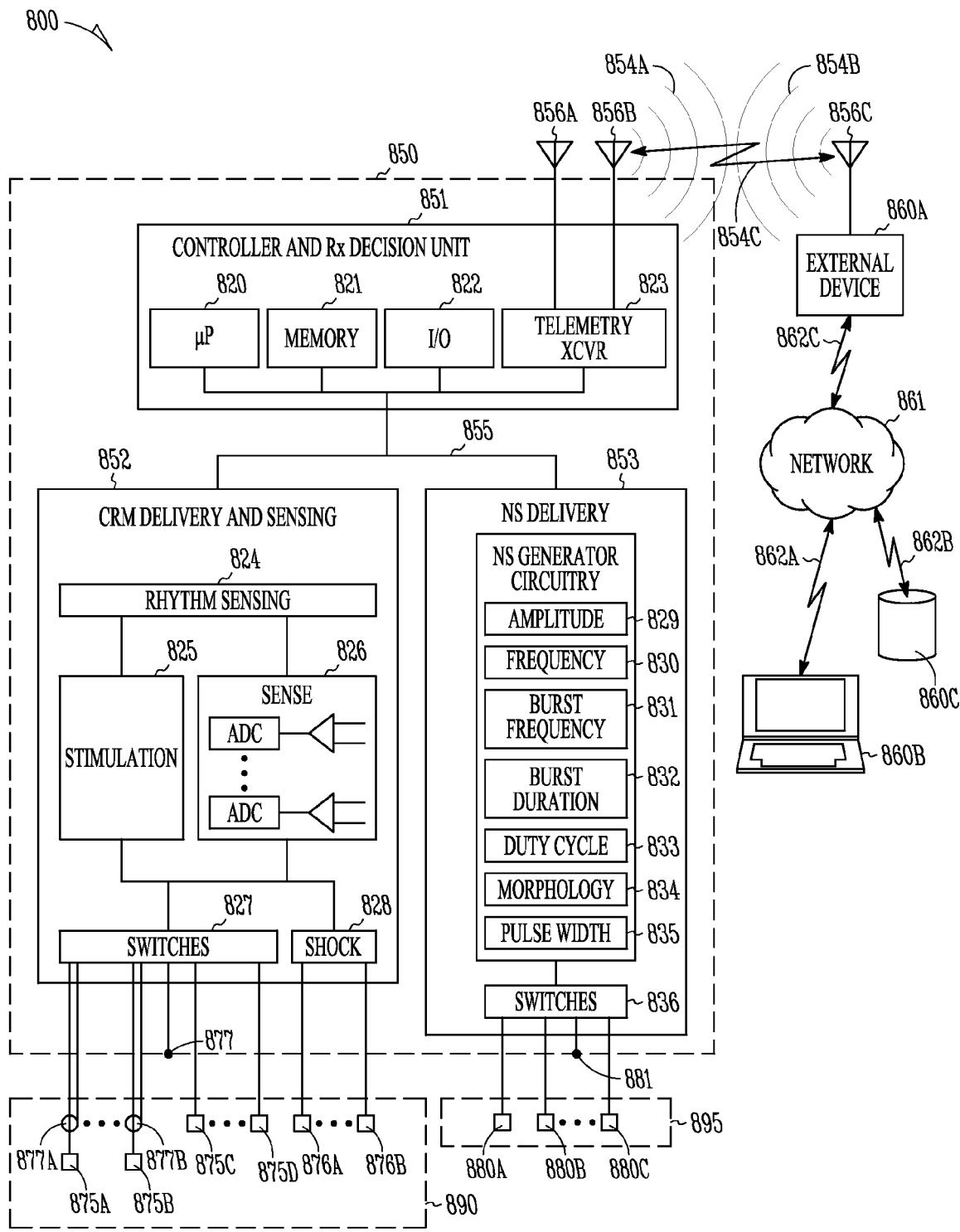
FIG. 8 is a diagram illustrating generally an example of at least a portion of a system that can include at least one cardiac rhythm management system, partially or completely implanted within a patient, coupled to an external device.

FIG. 8 is a diagram illustrating generally an example of at least a portion of a system 800 that can include at least one cardiac rhythm management system 850, partially or completely implanted within a patient, coupled to an external device 860A.

In the example of FIG. 8, a therapy controller and therapy decision unit 851 can be included in the CRM system 850. A communicative coupling 855 can be included between the therapy controller and therapy decision unit 851, CRM delivery and sensing circuit 852, and a neural stimulation generator 853. As shown in FIGS. 5, 7, in some examples, the neural stimulation generator 853 can be separate and distinct from the therapy controller 851 and CRM sensing and delivery circuit 852. In such an example, wireless communicative coupling 855 can be used, such as discussed above.

For examples where CRM sensing and delivery circuit 852, and neural stimulation generator 853 are physically separate assemblies, the controller 851 can be included the same housing as either CRM sensing and delivery circuit 852, or neural stimulation generator 853, or both (e.g., multiple controllers 851 can be included in the system 800), or neither, as in the example of an externally-located controller 851.

In the example shown in FIG. 8, the controller 851 can comprise a microprocessor 820, memory 821, input/output block 822, and a telemetry transceiver 823.

In some examples, the controller 851 can be physically implemented as, for example, a single co-integrated circuit, system-on-a-chip (SoC), multi-chip module, flexible or rigid circuit assembly, or the like. In some examples, the controller 851 can be logically realized as, for example, a microcontroller, programmable logic device (e.g., field programmable gate array), state machine, or the like.

In some examples, memory 821 can include volatile or non-volatile portions. In some examples, memory 821 and can include portions using error detection, error correction, or both.

In some examples, telemetry block 823 can include one or more wireless energy transducers 856A-B (e.g., antennas). In some examples, multiple individual antennas 856A-B can be included and selected between, such as for allowing various transduction techniques, and can allow the CRM system 850 to use more than one energy transduction technique for communication (e.g., a CRM system 850 can use magnetic and acoustic communication 854A-B when equipped with both a magnetic transducer 856A and, for example, an acoustic transducer 856B).

In the example of FIG. 8, CRM delivery and sensing 852 includes a rhythm sensor 824 to detect, classify, or discriminate between sensed arrhythmias. In some examples, a rhythm sensor 824, can include, for example, one or more comparators, event counters, timers or the like.

One or more leads 875A-D, 877A-B can include one or more respective electrodes that can be placed at one or more desired tissue locations 890 where an electrocardiogram can be sensed. Switches 827 can electrically couple unipolar lead channels 875C-D or bipolar lead channels 875A-B (e.g., "tip" conductors), 877A-B (e.g., "ring" conductors) to signal conditioning circuitry included in sensing block 826 or to a stimulus block 825. In some examples, a one-to-one correspondence can exist between stimulus block 825 outputs, sensing inputs 826, and leads 875A-D, 877A-B. In some examples, leads can be multiplexed, such as by using switches 827.

In FIG. 8, the sensing block 826 can include one or more analog-to-digital converters (ADCs). In some examples ADCs in the sense block 826 can digitize a sensed electrocardiogram for output to a rhythm sensor 824 for use in discriminating between arrhythmias.

For example, a rhythm sensor 824 can include a heart rate threshold comparator configured to compare a heart rate derived from a sensed electrogram provided by the sensing circuitry 826, to a stored heart rate threshold value. A heart rate that meets or exceeds this threshold value for a specified duration of time can be used by the rhythm sensor 824 to declare a probable ventricular tachycardia event. The controller 851 can respond, such as with one or more commands via communicative coupling 855, to provide appropriate therapy (e.g., ATP or shock 828).

In some examples, the rhythm sensor 824 can include a heart rate threshold comparator and one or more of a heart rate acceleration threshold comparator, a morphological feature comparator, or an R-R interval variance comparator, such as described above.

In some examples, the rhythm sensor 824 can include one or more of atrial or ventricular event counters (e.g., a counter can store a total number of atrial or ventricular electrogram threshold crossings during a specified time interval). The rhythm sensor 824 can include an event rate comparator, such as to compare the atrial event rate with the ventricular event rate to distinguish a ventricular arrhythmia from an atrial arrhythmia, such as described above.

In some examples, the rhythm sensor 824 can include a one-to-one correspondence detector configured to declare a probable SVT when an atrial event rate substantially equals a ventricular event rate.

In some examples, a rhythm sensor 824 can include an SVT discriminator. An SVT discriminator can include one or more heart rate threshold comparators, such as described above for ventricular tachyarrhythmia detection, to compare an atrial sensed event rate to a stored threshold value.

For example, when an atrial sensed event rate is less than or equal to a ventricular tachyarrhythmia heart rate threshold value, but meets or exceeds an atrial heart rate threshold, an SVT discriminator can use such a window comparison to declare a probable reentrant SVT. Controller 851 can respond, such as with one or more commands via communicative coupling 855 to provide appropriate therapy (e.g., neural stimulation to mediate or terminate the reentrant SVT).

In some examples, similar to the SVT discrimination described above, the rhythm sensor 824 can include a heart rate ratio comparator to compare a computed ratio of two instantaneous or aggregated measures of sensed heart rate to a stored heart rate threshold ratio.

In some examples, depending on whether the computed ratio is above, at, or below a specified ratio threshold value, an SVT can be classified as either atrial fibrillation or atrial flutter.

In some examples, comparators, event timers, discriminators, or event detectors in a rhythm sensor 824 can be triggered, enabled or disabled through either hardware or software control by the controller 851.

In some examples, a rhythm sensor 824 can include a heart rate acceleration comparator configured to compare a change in beat-to-beat intervals sampled at two or more times to a stored heart rate acceleration threshold value.

In some examples, individual unipolar lead channels 875C-D can be monitored (e.g., sensed) or stimulated, such as with respect to another lead 875A-D, 877A-B, or with respect to a can electrode 877 that is electrically coupled to a portion of the CRM device 850 housing.

In some examples, the CRM delivery and sensing circuit 852 can be included in an implantable pulse generator, and leads 875A-D, 877A-B can be intravascularly fed to an intracardiac location 890, and can provide independent sensing 826 of ventricular or atrial events (e.g., R-waves or P-waves) at selected intracardiac sites 890.

In some examples, CRM delivery or sensing circuit 852 includes defibrillation shock output circuit 828. In some examples, shock lead channels 876A-B are separate and distinct from channels 877A-B, 875A-D. In some examples, one or more of shock output circuit 828 or switch 827 can provide isolation such as between shock leads 876A-B, low voltage stimulus and sensing leads 877A-B, 875A-D, sensing circuitry 826 and stimulation circuitry 825.

Electrodes associated with shock lead channels 876A-B can be positioned to provide defibrillation to an atrial site 890, a ventricular site 890, or both. Pacing channels 877A-B, 875A-D, and shock channels 876A-B can be positioned provide electrical energy to one or more endocardial, epicardial or intravenous sites 890, or the like.

In the example of FIG. 8, a neural stimulation generator 853 includes excitation circuitry such as to provide one or more of a selected amplitude 829, frequency 830, burst frequency 831, burst duration 832, duty cycle 833, morphology 834, and pulse width 835 for neural stimulation coupled to one or more switches 836.

In the example of FIG. 8, switches 836 couple neural stimulation excitation circuitry to one or more stimulation leads 880A-C. As similarly discussed with respect to cardiac leads 875A-D, 877A-B, in neural electrostimulation, one or more neural stimulation leads 880A-C can selectively be excited such as with respect to one another (e.g., bipolar stimulation), or with respect to a can electrode 881. In some examples, individual neural stimulation generator circuits can drive individual outputs and can provide for concurrent, independent, programmable stimulation at two or more neural target sites 895. Alternatively, or in combination with one or more of the previous examples, the switches 836 can optionally provide for multiplexing of one or more neural stimulation leads 880A-C to a given neural stimulation excitation circuit.

In some examples, the controller 851 can command a neural stimulation delivery, such as via communicative coupling 855, cardio-synchronously as sensed events occurring at a tissue site 890 are detected by sensing circuitry 826 included in the CRM delivery and sensing circuit 852 (e.g., synchronizing one or more neural stimulation bursts with respect to one or more cardiac events).

By way of illustrative example, but not by way of limitation, six bursts can be delivered during about a one minute stimulation time, and the length of each burst can be about five seconds. For this example, the burst frequency 831 can be six bursts-per-minute, the stimulation time or burst duration 832 can be 60 seconds, and the duty cycle 833 can be 50%.

In some examples, the duty cycle 833 can be modulated, such as by using an inter-burst interval (e.g., burst frequency 831) that varies from one burst to another, or by modulating the intra-burst pulse-width, or a combination of both.

Morphology 834 can refer to the shape of the amplitude envelope of a burst, or an individual cycle within the burst, and can include, but is not restricted to, square wave, triangle wave, sinusoidal, raised cosine (e.g., haversine), a band-limited noise characteristic selected to mimic naturally-occurring stimulation, or the like.

In the example of FIG. 8, an external device 860A can be communicatively coupled to the CRM system 850, such as via a wireless communication transducer 856C.

As similarly described in the context of FIGS. 5, 7, in some examples the wireless signal 854C can be used for transmitting or receiving one or more of status, diagnostic, control or informational messages between the CRM system 850 and external device 860A. Alternatively, or additionally, in some examples, transducer 856C can supply some or all operating energy 854B to one or more implanted functional blocks of the CRM system 851.

Examples of external devices 860A can include, but are not limited to, physician or clinician programmers, bedside monitors, personal digital assistants (PDAs), remote follow-up devices, hospital room equipment (e.g., monitoring equipment), operating theatre devices (e.g., acute stimulation devices, pacing system analyzers), or the like.

In the example of FIG. 8, an external device 860A can be communicatively coupled 862A-C through a network 861 to a terminal 860B (e.g., a laptop, PDA, or desktop computer connected via a communicative coupling 862A to network 861), and to a network storage device or server 860C.

In some examples, one or more of a clinician, physician, or a patient, or other user can access information transferred from or to CRM system 850, such as through retrieval from storage 860C or from external device 860A. In some examples, communication between terminal 860B and CRM device 850 can occur in near real-time, such as during a physician follow-up.

In some examples, such as in using a remote patient management system, follow-up can occur by a clinician or physician using terminal 860B, which can even be in an off-line manner without requiring a real-time communicative connection to external device 860A or to CRM device 850.

FIG. 9 is a diagram 900 illustrating generally an example of at least a portion of an event timeline 950 indicating, not to scale, a relative order of atrial 912, 922A-C, 932A-C sensed events and ventricular 914A-B, 924A-C, 934 sensed events in various arrhythmia detection scenarios 910, 920, 930.

In an example, a scenario 910 as shown in FIG. 9 can occur during a ventricular tachyarrhythmia. A functional block within a CRM device, such as a rhythm sensor as discussed in the context of FIG. 8, can detect a ventricular sense event 914B occurring within an interval 916. In some examples, the interval 916 can be specified programmatically to correspond to a tachycardia rate threshold value. The absence of an atrial sense event during interval 916 can indicate a lack of one-to-one correspondence between atrial and ventricular sensed events, and can indicate a ventricular event rate greater than an atrial event rate. Such indications can allow a functional block in a CRM device, such as a rhythm sensor, to declare a probable ventricular tachyarrhythmia.

In an example, a scenario 920 as shown in FIG. 9 can occur during an atrial tachyarrhythmia. High rate atrial sense events 922A-C can be followed by corresponding ventricular sense events 924A-C. Each atrial event, such as, for example 922A, can be followed by one and only one corresponding ventricular event, for example, 924A. A one-to-one correspondence between atrial and ventricular sensed events can be detected by, for example, a rhythm sensor, and a probable SVT can be declared. A controller can inhibit ventricular shock therapy in response to a declaration of a probable SVT.

In an example, a scenario 930 as shown in FIG. 9 can occur during an atrial tachyarrhythmia. High rate atrial sense events 932A-C and an absence of a ventricular sense event 934 between atrial sense events 932A-B and 932B-C can indicate a lack of a one-to-one correspondence between atrial and ventricular events, and an atrial event rate greater than a ventricular event rate. Such indications can allow a functional block in CRM device, such as a rhythm sensor, to declare a probable SVT. A controller can inhibit ventricular shock therapy in response to a declaration of a probable SVT.

Figure 10:
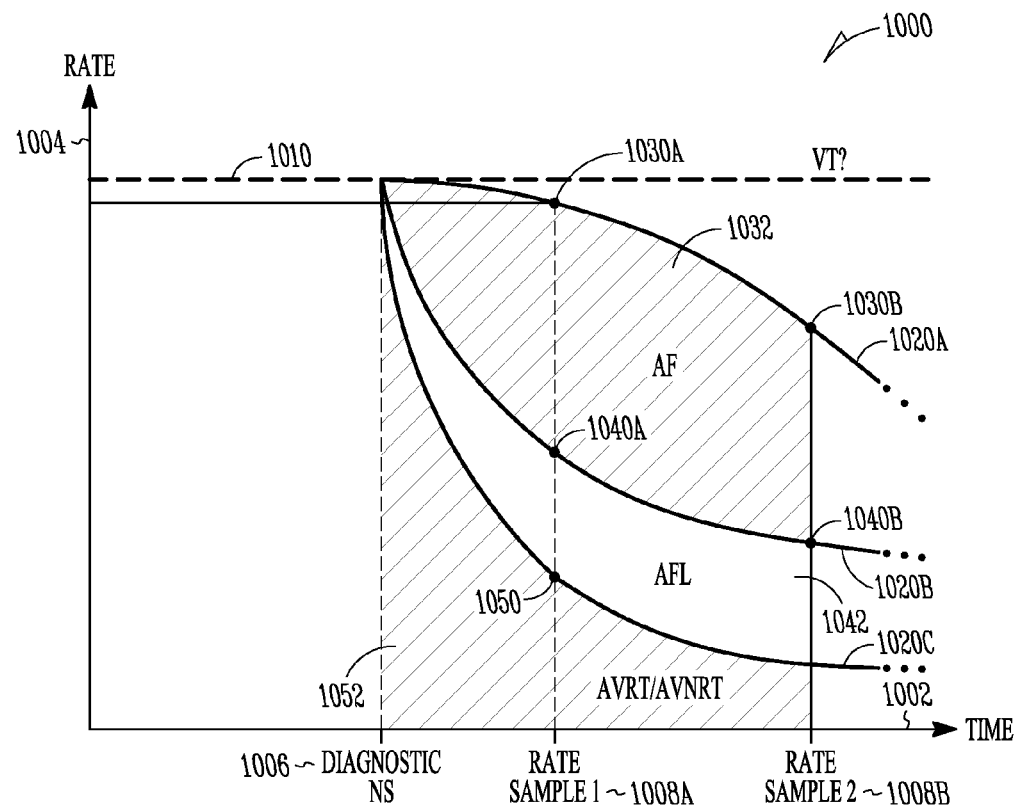
FIG. 10 is a diagram illustrating generally an example of a plot of various arrhythmia classification rules with respect to a cardiac event rate and time.

FIG. 10 is a diagram illustrating generally an example of a plot 1000 of various arrhythmia classification rules 1032, 1042, 1052 with respect to a cardiac event rate 1004 (e.g., heart rate) and time 1002.

In some examples, at a time before delivering a diagnostic neural stimulation 1006, a high atrial sensed event rate 1010 has been detected. At 1006, a diagnostic neural stimulation can be applied, and just afterward, a first rate sample 1008A can then be made. If the rate sample 1008A equals or exceeds a ventricular tachyarrhythmia/atrial fibrillation region boundary 1030A defined by rate change threshold curve 1020A, a CRM system can declare a probable ventricular arrhythmia or an indeterminate atrial tachycardia. In some examples, to provide greater patient safety, a CRM system controller can provide shock therapy in response to a probable VT declaration when an upper rate threshold defined by region boundary 1030A is met, or exceeded by a specified amount. Since VT can exhibit a heart rate that can overlap with other arrhythmias, VT can also be discriminated from SVTs by, for example, a lack of a detectable change in rate at rate samples 1008A, or 1008B, or both, after diagnostic neural stimulation 1006.

In another example, if the rate sample 1008A is (1) less than or equal to the ventricular tachyarrhythmia/atrial fibrillation region boundary 1030A, and (2) at or above the atrial flutter/atrial fibrillation boundary 1040 defined by the rate change threshold curve 1020B, a CRM system can declare probable atrial fibrillation. In some examples, boundary 1040A can be established as a threshold ratio of the rate sample 1008A (e.g., atrial heart rate) to the event rate 1010 before delivering the diagnostic neural stimulation at 1006. In some examples, the threshold ratio can be 1/2 or 2/3.

For instance, an atrial sensed event rate (e.g., atrial heart rate) at 1010 is 300 beats-per-minute (bpm), before delivering the diagnostic neural stimulation. The atrial rate is also below an upper rate threshold defined by region boundary 1030A. After delivering diagnostic neural stimulation 1006, the rate sample 1008A is at or above 200 bpm. If a threshold ratio of 2/3 is used, the lower rate threshold defined by region boundary 1040A is 200 bpm, and a CRM system can declare the arrhythmia as probable atrial fibrillation.

Atrial fibrillation can exhibit a gradual decrease 1020A in heart rate after a diagnostic neural stimulation at 1006. In some examples, atrial shock can be suppressed until a later rate sample 1008B to confirm the atrial fibrillation determination. In some examples, the region boundaries 1030A, 1040A during the repeat/confirmation test can remain the same as the previous test.

In some examples, a confirmation made at rate sample 1008B can apply a lower threshold corresponding to region boundaries 1030B, 1040B, or both, than the initial determination. This enhances patient safety, since a lower threshold increases the likelihood that atrial or ventricular shock therapy can be provided by a controller in response to an atrial fibrillation or ventricular tachyarrhythmia declaration.

In another example, if rate sample 1008A is less than or equal to the atrial flutter/AVRT/AVNRT region boundary 1050 such as established by the rate change threshold curve 1020C, then the CRM system can declare the arrhythmia as a probable reentrant SVT. In an example, reentrant atrial arrhythmias that terminate spontaneously or as a result of the diagnostic neural stimulation can also be declared as probable reentrant SVTs.

In some examples, cardiac event rates or morphological features associated with atrial or ventricular sensed electrograms, or both, can be used to classify SVTs in a manner similar to FIG. 10. For example, atrio-ventricular delay (AVD), or its inverse, can be sampled and a corresponding degree, or rate of change, or the like, in AVD after neural stimulation can be used to classify an SVT, or to discriminate between an SVT and VT, or both.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), or the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system, comprising:
a sensing input configured to sense a tachyarrhythmia;
a rhythm sensor, coupled to the sensing input, configured to:
   compare a sensed tachyarrhythmia with a ventricular tachyarrhythmia criterion; and
   compare a sustained tachyarrhythmia with a supraventricular tachyarrhythmia (SVT) criterion in response to the tachyarrhythmia continuing during or after a diagnostic neural stimulation;
a neural stimulation generator, coupled to the rhythm sensor, configured to provide the diagnostic neural stimulation in response to a determination that the sensed tachyarrhythmia does not satisfy the ventricular tachyarrhythmia criterion; and
a ventricular tachyarrhythmia therapy generator, coupled to the rhythm sensor, configured to:
   provide a ventricular tachyarrhythmia therapy in response to a determination that the sensed tachyarrhythmia satisfies the ventricular tachyarrhythmia criterion; and
   provide a ventricular tachyarrhythmia therapy in response to a determination that the sensed tachyarrhythmia does not satisfy the SVT criterion.

2. The system of claim 1, wherein the ventricular tachyarrhythmia criterion included in the rhythm sensor includes at least one comparator selected from the list of:
(1) a heart rate threshold comparator, coupled to the sensing input;
(2) a heart rate acceleration comparator, coupled to the sensing input;
(3) a morphological feature comparator, coupled to the sensing input; and
(4) an R-R interval variance comparator, coupled to the sensing input.

3. The system of claim 2, wherein:
(1) the heart rate threshold comparator is configured to compare a sensed heart rate with a heart rate threshold value, and wherein the heart rate threshold comparator is configured to declare a probable ventricular tachyarrhythmia when the heart rate threshold is met or exceeded continuously during an interval equal to or longer than a timeout limit;
(2) the heart rate acceleration comparator is configured to compare a sensed heart rate acceleration with a heart rate acceleration threshold value, and wherein the heart rate acceleration comparator is configured to declare a probable ventricular tachyarrhythmia when the heart rate acceleration threshold is met or exceeded;
(3) the morphological feature comparator is configured to compare a sensed tachyarrhythmia with an electrogram morphological feature template, and wherein the comparator is configured to declare a probable ventricular tachyarrhythmia when the morphological feature comparison threshold is met or exceeded; and
(4) the R-R interval variance comparator is configured to compare the variance of a population of sensed R-R intervals with a stability threshold variance, and wherein the comparator is configured to declare a probable ventricular tachyarrhythmia when the stability threshold variance is not met or exceeded by the variance of a population of sensed R-R intervals.

4. The system of claim 1, wherein the sensing input is configured to sense an atrial event rate and a ventricular event rate, and wherein the SVT criterion included in the rhythm sensor comprises an event rate comparator, coupled to the sensing input, the event rate comparator configured to declare the SVT criterion as satisfied by the sensed tachyarrhythmia when a sensed atrial event rate is greater than or equal to a sensed ventricular event rate by a specified amount.

5. The system of claim 1, wherein the sensing input is configured to sense an atrial event and a ventricular event, and wherein the SVT criterion included in the rhythm sensor comprises a one-to-one correspondence detector, coupled to the sensing input, the one-to-one correspondence detector configured to declare the SVT criterion as satisfied by the sensed tachyarrhythmia when a one-to-correspondence between an atrial event and a ventricular event is detected.

6. The system of claim 1, comprising a rhythm sensor configured to trend a cardiac event rate over time, wherein the rhythm sensor includes an SVT discriminator, the SVT discriminator configured to:
   classify an SVT as a probable reentrant SVT when a rate trend corresponds to a reentrant SVT criterion;
   classify an SVT as probable atrial flutter (AFL) when the rate trend corresponds to an atrial flutter criterion; and
   classify an SVT as atrial fibrillation (AF) when the rate trend corresponds to an atrial fibrillation criterion.

7. The system of claim 6, wherein the SVT discriminator is configured to sense a termination of a tachyarrhythmia during or after a neural stimulation.

8. The system of claim 6, comprising:
an SVT discriminator including a probable reentrant SVT criterion, the SVT discriminator comprising:
   a heart rate threshold comparator, coupled to the sensing input, configured to compare a sensed heart rate with a heart rate threshold value, and wherein the heart rate threshold comparator is configured to classify an SVT as a probable reentrant SVT when, after a neural stimulation, the sensed heart rate is below the heart rate threshold value; and
   a therapy decision unit, coupled to the SVT discriminator, configured to select a therapeutic neural stimulation protocol for terminating the probable reentrant SVT, in response to the classification of an SVT as a probable reentrant SVT;
wherein the neural stimulation generator is coupled to the therapy decision unit and configured to deliver the selected therapeutic neural stimulation protocol.

9. The system of claim 6, comprising:
an SVT discriminator including a probable atrial flutter criterion, the SVT discriminator comprising:
   a heart rate ratio comparator, coupled to the sensing input, configured to compare a computed ratio of two sensed heart rates with a threshold ratio value, the two sensed heart rates sampled after a neural stimulation, and wherein the heart rate ratio comparator is configured to classify an SVT as a probable atrial flutter when the computed ratio is below the threshold ratio value.

10. The system of claim 9, comprising:
a therapy decision unit, coupled to the SVT discriminator, configured to select a neural stimulation protocol for terminating the probable atrial flutter and to optionally select an anti-tachyarrhythmia pacing (ATP) protocol for terminating the probable atrial flutter, in response to the classification of an SVT as a probable atrial flutter; and
an ATP stimulation generator, coupled to the therapy decision unit, configured to optionally deliver the selected ATP protocol;
wherein the neural stimulation generator is coupled to the therapy decision unit and configured to deliver the selected neural stimulation protocol.

11. The system of claim 6, comprising:
an SVT discriminator including a probable atrial fibrillation criterion, the SVT discriminator comprising:
a heart rate ratio comparator, coupled to the sensing input, configured to compare a computed ratio of two sensed heart rates with a threshold ratio value, the two sensed heart rates sampled after a neural stimulation, and wherein the heart rate ratio comparator is configured to classify an SVT as a probable atrial fibrillation when the computed ratio is at or above the threshold ratio value.

12. The system of claim 11, comprising:
a therapy decision unit, coupled to the SVT discriminator, configured to select a neural stimulation protocol for terminating the probable atrial fibrillation and to optionally select an atrial shock protocol for terminating the probable atrial fibrillation, in response to the classification of an SVT as a probable atrial fibrillation; and
an atrial shock generator, coupled to the therapy decision unit, configured to optionally deliver the selected atrial shock protocol;
wherein the neural stimulation generator is coupled to the therapy decision unit and configured to deliver the selected neural stimulation protocol.

13. A method comprising:
sensing a tachyarrhythmia;
comparing the sensed tachyarrhythmia with a ventricular tachyarrhythmia criterion;
providing a ventricular tachyarrhythmia therapy in response to determining that the sensed tachyarrhythmia satisfies the ventricular tachyarrhythmia criterion;
providing a diagnostic neural stimulation in response to determining that the sensed tachyarrhythmia does not satisfy the ventricular tachyarrhythmia criterion;
determining whether the tachyarrhythmia continues during or after the diagnostic neural stimulation when the tachyarrhythmia is sustained;
comparing the tachyarrhythmia sensed during or after the diagnostic neural stimulation with a supraventricular tachyarrhythmia (SVT) criterion; and
providing a ventricular tachyarrhythmia therapy in response to determining that the sensed tachyarrhythmia does not satisfy the SVT criterion.

14. The method of claim 13, wherein satisfying the ventricular tachyarrhythmia criterion includes satisfying at least one criterion selected from the list of:
(1) a heart rate threshold criterion;
(2) a heart rate acceleration criterion;
(3) an electrogram morphological feature template criterion; and
(4) an R-R interval stability criterion.

15. The method of claim 14, wherein:
(1) the heart rate threshold criterion comprises:
establishing a heart rate threshold;
comparing a sensed heart rate to the heart rate threshold;
triggering a timer when the patient heart rate meets or exceeds the heart rate threshold;
establishing a timeout limit;
comparing an elapsed time indicated by the timer with the timeout limit; and
declaring the sensed tachyarrhythmia as a probable ventricular tachyarrhythmia when the heart rate threshold is met or exceeded continuously during an interval equal to or longer than the timeout limit;
(2) the heart rate acceleration criterion comprises:
establishing a heart rate acceleration threshold;
comparing a sensed heart rate acceleration to the heart rate acceleration threshold; and
declaring the sensed tachyarrhythmia as a probable ventricular tachyarrhythmia when the heart rate acceleration threshold is met or exceeded;
(3) the electrogram morphological feature template criterion comprises:
establishing an electrogram morphological feature template for ventricular tachyarrhythmia;
establishing a morphological comparison threshold;
comparing the sensed tachyarrhythmia to the electrogram morphological feature template; and
declaring the sensed tachyarrhythmia as a probable ventricular tachyarrhythmia when the morphological comparison threshold is met or exceeded; and
(4) the R-R interval stability criterion comprises:
sensing a series of R-R intervals;
extracting a variance of a population of sensed R-R intervals;
establishing a stability threshold variance;
comparing the variance of the population of sensed R-R intervals to the stability threshold variance; and
declaring the sensed tachyarrhythmia as a probable ventricular tachyarrhythmia when the variance of a population of sensed R-R intervals fail to meet or exceed the stability threshold variance.

16. The method of claim 13, wherein satisfying the SVT criterion includes sensing an atrial event rate greater than or equal to a ventricular event rate.

17. The method of claim 13, wherein satisfying the SVT criterion includes sensing a substantially one-to-one correspondence between an atrial event and a ventricular event.

18. The method of claim 13, comprising:
trending a cardiac event rate over time;
classifying an SVT as a probable reentrant SVT when a rate trend corresponds to a reentrant SVT criterion;
classifying an SVT as probable atrial flutter (AFL) when the rate trend corresponds to an atrial flutter criterion; and
classifying an SVT as atrial fibrillation (AF) when the rate trend corresponds to an atrial fibrillation criterion.

19. The method of claim 18, wherein the reentrant SVT criterion includes sensing a termination of a tachyarrhythmia during or after the providing the diagnostic neural stimulation.

20. The method of claim 18, comprising:
selecting a neural stimulation protocol configured for terminating the probable reentrant SVT;
providing a therapeutic neural stimulation configured for terminating the probable reentrant SVT when the sensed tachyarrhythmia satisfies a reentrant SVT criterion; and
wherein the reentrant SVT criterion includes:
establishing a lower threshold value for a heart rate;
sampling the heart rate at a specified time after the providing the therapeutic neural stimulation;

comparing the sampled heart rate with the lower threshold value; and
detecting the sampled heart rate below the lower threshold value.

21. The method of claim 18, wherein the probable atrial flutter criterion includes:
establishing a threshold ratio value for a heart rate;
sampling the heart rate at two specified times;
dividing a later sample of the value of the heart rate by an earlier sample of the value of the heart rate to establish a computed ratio;
comparing the computed ratio with the threshold ratio value; and
detecting a ratio below the threshold ratio value.

22. The method of claim 21, comprising:
selecting a neural stimulation protocol for terminating the probable atrial flutter;
providing a therapeutic neural stimulation selected for terminating the probable atrial flutter when the sensed tachyarrhythmia satisfies the probable atrial flutter criterion; and
optionally providing anti-tachyarrhythmia pacing (ATP) for terminating the probable atrial flutter when the sensed tachyarrhythmia satisfies the probable atrial flutter criterion.

23. The method of claim 18, wherein the probable atrial fibrillation criterion includes:
establishing a threshold ratio value for a heart rate;
sampling the heart rate at two specified times;
dividing a later sample of the value of the heart rate by an earlier sample of the value of the heart rate to establish a computed ratio;
comparing the computed ratio with the threshold ratio value; and
detecting a ratio at or above the threshold ratio value.

24. The method of claim 23 comprising:
selecting a neural stimulation protocol for terminating the probable atrial fibrillation;
providing a therapeutic neural stimulation selected for terminating the probable atrial fibrillation when the sensed tachyarrhythmia satisfies the probable atrial fibrillation criterion; and
optionally providing atrial shock therapy for terminating the probable atrial fibrillation when the sensed tachyarrhythmia satisfies the probable atrial fibrillation criterion.

25. A machine readable medium including instructions that, when performed by the machine, cause the machine to:
sense a tachyarrhythmia;
compare the sensed tachyarrhythmia with a ventricular tachyarrhythmia criterion;
provide a ventricular tachyarrhythmia therapy in response to determining that the sensed tachyarrhythmia satisfies the ventricular tachyarrhythmia criterion;
provide a diagnostic neural stimulation in response to determining that the sensed tachyarrhythmia does not satisfy the ventricular tachyarrhythmia criterion;
determine whether the tachyarrhythmia continues during or after the diagnostic neural stimulation when the tachyarrhythmia is sustained;
compare the tachyarrhythmia sensed during or after the diagnostic neural stimulation with a supraventricular tachyarrhythmia (SVT) criterion; and
provide a ventricular tachyarrhythmia therapy in response to determining that the sensed tachyarrhythmia does not satisfy the SVT criterion.

* * * * *